US009662486B2

(12) United States Patent
Harris et al.

(10) Patent No.: US 9,662,486 B2
(45) Date of Patent: *May 30, 2017

(54) METHODS AND DEVICES FOR ACTIVATING BROWN ADIPOSE TISSUE USING ELECTRICAL ENERGY

(71) Applicants: Ethicon-Endo Surgery, Inc., Cincinatti, OH (US); The General Hospital Corporation, Boston, MA (US)

(72) Inventors: Jason L. Harris, Lebanon, OH (US); Nicholas Stylopoulos, Swampscott, MA (US); Lee M. Kaplan, Boston, MA (US); Tamara C. Baynham, Bowie, MD (US); Taylor W. Aronhalt, Loveland, OH (US)

(73) Assignees: Ethicon Endo-Surgery, Inc., Cincinnati, OH (US); The General Hospital, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/700,611

(22) Filed: Apr. 30, 2015

(65) Prior Publication Data

US 2015/0258326 A1 Sep. 17, 2015

Related U.S. Application Data

(63) Continuation of application No. 12/980,659, filed on Dec. 29, 2010, now Pat. No. 9,044,606.
(Continued)

(51) Int. Cl.
*A61N 1/36* (2006.01)
*A61N 1/05* (2006.01)
*A61N 1/04* (2006.01)

(52) U.S. Cl.
CPC ......... *A61N 1/0456* (2013.01); *A61N 1/0504* (2013.01); *A61N 1/36* (2013.01);
(Continued)

(58) Field of Classification Search
CPC . A61N 1/0504; A61N 1/3606; A61N 1/36014
See application file for complete search history.

(56) References Cited

U.S. PATENT DOCUMENTS

| 4,498,843 A | 2/1985 | Schneider et al. |
| 4,578,770 A | 3/1986 | Mitani |

(Continued)

FOREIGN PATENT DOCUMENTS

| CN | 2045308 U | 10/1989 |
| CN | 2520883 Y | 11/2002 |

(Continued)

OTHER PUBLICATIONS

Jaiswal, N. et al., "Osteogenic differentiation of purified, culture-expanded human mesenchymal stem cells in vitro," J. Cell Biochem. (1997) 64(2): 295-312.
(Continued)

*Primary Examiner* — William Levicky
(74) *Attorney, Agent, or Firm* — Mintz Levin Cohn Ferris Glovsky and Popeo, P.C.

(57) ABSTRACT

Methods and devices are provided for activating brown adipose tissue (BAT). Generally, the methods and devices can activate BAT to increase thermogenesis, e.g., increase heat production in the patient, which over time can lead to weight loss. In one embodiment, a medical device is provided that activates BAT by electrically stimulating nerves that activate the BAT and/or electrically stimulating brown adipocytes directly, thereby increasing thermogenesis in the BAT and inducing weight loss through energy expenditure.

35 Claims, 11 Drawing Sheets

Related U.S. Application Data

(60) Provisional application No. 61/297,405, filed on Jan. 22, 2010.

(52) U.S. Cl.
CPC ......... *A61N 1/3605* (2013.01); *A61N 1/3606* (2013.01); *A61N 1/36014* (2013.01); *A61N 1/36153* (2013.01); *A61N 1/36157* (2013.01); *A61N 1/36171* (2013.01); *A61N 1/36192* (2013.01)

(56) References Cited

U.S. PATENT DOCUMENTS

| | | | |
|---|---|---|---|
| 4,596,792 A | 6/1986 | Vyas | |
| 4,599,230 A | 7/1986 | Milich et al. | |
| 4,599,231 A | 7/1986 | Milich et al. | |
| 4,601,903 A | 7/1986 | Frasch | |
| 4,608,251 A | 8/1986 | Mia | |
| 4,772,631 A | 9/1988 | Holloway et al. | |
| 4,927,836 A | 5/1990 | Holloway et al. | |
| 4,937,267 A | 6/1990 | Holloway et al. | |
| 4,978,338 A | 12/1990 | Melsky et al. | |
| 5,434,184 A | 7/1995 | Holloway et al. | |
| 5,453,270 A | 9/1995 | Bills | |
| 5,486,359 A | 1/1996 | Caplan et al. | |
| 5,724,996 A | 3/1998 | Piunti | |
| 5,731,408 A | 3/1998 | Hadley et al. | |
| 5,736,396 A | 4/1998 | Bruder et al. | |
| 5,789,654 A | 8/1998 | Lowell et al. | |
| 5,811,094 A | 9/1998 | Caplan et al. | |
| 5,827,735 A | 10/1998 | Young et al. | |
| 5,827,740 A | 10/1998 | Pittenger | |
| 5,837,539 A | 11/1998 | Caplan et al. | |
| 5,837,670 A | 11/1998 | Hartshorn | |
| 5,843,723 A | 12/1998 | Dubensky, Jr. et al. | |
| 5,911,992 A | 6/1999 | Braswell et al. | |
| 6,069,147 A | 5/2000 | Williams et al. | |
| 6,071,747 A | 6/2000 | Strosberg et al. | |
| 6,072,100 A | 6/2000 | Mooney et al. | |
| 6,197,580 B1 | 3/2001 | Sususlic et al. | |
| 6,207,878 B1 | 3/2001 | Campbell et al. | |
| 6,224,873 B1 | 5/2001 | Jones | |
| 6,246,912 B1* | 6/2001 | Sluijter | A61N 1/36017 607/100 |
| 6,381,496 B1* | 4/2002 | Meadows | A61N 1/08 607/59 |
| 6,445,955 B1 | 9/2002 | Michelson et al. | |
| 6,451,336 B2 | 9/2002 | Sugano et al. | |
| 6,475,530 B1 | 11/2002 | Kuhrts | |
| 6,532,386 B2 | 3/2003 | Sun et al. | |
| 6,565,847 B1 | 5/2003 | Gorsek | |
| 6,602,694 B1 | 8/2003 | Albrandt et al. | |
| 6,605,297 B2 | 8/2003 | Nadachi et al. | |
| 6,620,594 B1 | 9/2003 | Giacobino et al. | |
| 6,645,229 B2 | 11/2003 | Matsumura et al. | |
| 6,694,185 B2 | 2/2004 | Orton | |
| 6,908,987 B2 | 6/2005 | Spiegelman et al. | |
| 6,922,590 B1 | 7/2005 | Whitehurst | |
| 6,927,288 B2 | 8/2005 | Ito | |
| 6,983,753 B1 | 1/2006 | Lenhard et al. | |
| 7,060,437 B1 | 6/2006 | Kopchick | |
| 7,091,006 B2 | 8/2006 | Spiegelman et al. | |
| 7,135,611 B2 | 11/2006 | MacDougald et al. | |
| 7,191,007 B2 | 3/2007 | Desai et al. | |
| 7,250,283 B2 | 7/2007 | Spiegelman et al. | |
| 7,264,602 B1 | 9/2007 | Longsworth | |
| 7,300,409 B2 | 11/2007 | Kopanic, Jr. et al. | |
| 7,367,341 B2 | 5/2008 | Anderson et al. | |
| 7,396,642 B2 | 7/2008 | Yamaoka et al. | |
| 7,440,806 B1 | 10/2008 | Whitehurst et al. | |
| 7,476,406 B1 | 1/2009 | Smidt | |
| 7,526,061 B2 | 4/2009 | Kobayashi | |
| 7,576,052 B2 | 8/2009 | Kahn et al. | |
| 7,599,736 B2 | 10/2009 | DiLorenzo | |
| 7,599,743 B2 | 10/2009 | Hassler, Jr. et al. | |
| 7,599,744 B2 | 10/2009 | Giordano et al. | |
| 7,647,112 B2 | 1/2010 | Tracey et al. | |
| 7,818,060 B2 | 10/2010 | Torgerson | |
| 7,935,073 B2 | 5/2011 | Levine et al. | |
| 7,979,137 B2 | 7/2011 | Tracey et al. | |
| 8,690,934 B2 | 4/2014 | Boyden et al. | |
| 9,044,606 B2 | 6/2015 | Harris et al. | |
| 2001/0014815 A1 | 8/2001 | Matsumura et al. | |
| 2001/0032337 A1 | 10/2001 | Forman | |
| 2002/0016618 A1* | 2/2002 | Da Silva | A61N 1/0472 607/72 |
| 2003/0082168 A1 | 5/2003 | Yegorova | |
| 2003/0104081 A1 | 6/2003 | Rombi | |
| 2003/0119775 A1 | 6/2003 | Surwit et al. | |
| 2003/0181958 A1* | 9/2003 | Dobak, III | A61N 1/36085 607/58 |
| 2003/0212016 A1 | 11/2003 | Gimeno et al. | |
| 2003/0220238 A1 | 11/2003 | Adams et al. | |
| 2004/0039312 A1* | 2/2004 | Hillstead | A61N 7/02 601/2 |
| 2004/0077556 A1 | 4/2004 | Chinery | |
| 2005/0043524 A1 | 2/2005 | Bhanot et al. | |
| 2005/0045498 A1 | 3/2005 | Purcell et al. | |
| 2005/0080026 A1 | 4/2005 | Steuernagel et al. | |
| 2005/0136429 A1 | 6/2005 | Guarente et al. | |
| 2005/0177067 A1 | 8/2005 | Tracey et al. | |
| 2005/0261223 A1 | 11/2005 | Czech et al. | |
| 2005/0277998 A1 | 12/2005 | Tracey et al. | |
| 2005/0288740 A1 | 12/2005 | Hassler et al. | |
| 2006/0004421 A1* | 1/2006 | Bennett | A61N 1/08 607/41 |
| 2006/0008540 A1 | 1/2006 | Xiu | |
| 2006/0014178 A1 | 1/2006 | Whitson et al. | |
| 2006/0084637 A1 | 4/2006 | Alemany | |
| 2006/0121158 A1 | 6/2006 | Ferruzzi et al. | |
| 2006/0195145 A1 | 8/2006 | Lee et al. | |
| 2006/0195146 A1 | 8/2006 | Tracey et al. | |
| 2006/0195153 A1 | 8/2006 | DiUbaldi et al. | |
| 2006/0204599 A1 | 9/2006 | Wheat | |
| 2006/0223104 A1 | 10/2006 | Kahn et al. | |
| 2007/0055154 A1 | 3/2007 | Torbati | |
| 2007/0162085 A1 | 7/2007 | DiLorenzo | |
| 2007/0185541 A1 | 8/2007 | DiUbaldi et al. | |
| 2007/0282318 A1 | 12/2007 | Spooner et al. | |
| 2008/0046012 A1 | 2/2008 | Covalin et al. | |
| 2008/0080026 A1 | 4/2008 | Mestha et al. | |
| 2008/0132962 A1 | 6/2008 | DiUbaldi et al. | |
| 2008/0138449 A1 | 6/2008 | Heuer et al. | |
| 2008/0139875 A1 | 6/2008 | Tracey et al. | |
| 2008/0147146 A1 | 6/2008 | Wahlgren et al. | |
| 2008/0262411 A1 | 10/2008 | Dobak | |
| 2008/0293830 A1 | 11/2008 | Katagiri et al. | |
| 2009/0012555 A1 | 1/2009 | Makower et al. | |
| 2009/0018594 A1 | 1/2009 | Laufer et al. | |
| 2009/0024144 A1 | 1/2009 | Zeiner et al. | |
| 2009/0024192 A1* | 1/2009 | Mulholland | A61B 18/1477 607/99 |
| 2009/0054487 A1 | 2/2009 | Kolonics et al. | |
| 2009/0062193 A1 | 3/2009 | Weyer et al. | |
| 2009/0081715 A1 | 3/2009 | Burns-Guydish et al. | |
| 2009/0093858 A1 | 4/2009 | DiUbaldi | |
| 2009/0118780 A1 | 5/2009 | DiLorenzo | |
| 2009/0132018 A1 | 5/2009 | DiUbaldi et al. | |
| 2009/0149918 A1 | 6/2009 | Krulevitch et al. | |
| 2009/0157149 A1 | 6/2009 | Wahlgren et al. | |
| 2009/0171375 A1 | 7/2009 | Coe et al. | |
| 2009/0202387 A1 | 8/2009 | Dlugos, Jr. et al. | |
| 2009/0202659 A1 | 8/2009 | Gimble | |
| 2009/0204131 A1 | 8/2009 | Ortiz et al. | |
| 2009/0228078 A1 | 9/2009 | Zhang et al. | |
| 2009/0306739 A1 | 12/2009 | DiLorenzo | |
| 2010/0056433 A1 | 3/2010 | Sensfuss | |
| 2010/0056948 A1 | 3/2010 | Hornby et al. | |
| 2010/0161001 A1 | 6/2010 | DiUbaldi et al. | |
| 2010/0161005 A1 | 6/2010 | Wahlgren et al. | |
| 2010/0222734 A1 | 9/2010 | Jayes et al. | |
| 2010/0239648 A1 | 9/2010 | Smith et al. | |
| 2010/0249677 A1 | 9/2010 | DiUbaldi et al. | |

(56) References Cited

U.S. PATENT DOCUMENTS

| | | | |
|---|---|---|---|
| 2010/0312295 A1* | 12/2010 | Vase | A61N 1/0551 607/2 |
| 2011/0094773 A1 | 4/2011 | Bare et al. | |
| 2011/0144490 A1 | 6/2011 | Davis et al. | |
| 2011/0152987 A1 | 6/2011 | Wahlgren et al. | |
| 2011/0237922 A1 | 9/2011 | Parker, III et al. | |
| 2011/0263490 A1 | 10/2011 | Kaplan et al. | |
| 2013/0110220 A1 | 5/2013 | Brown | |

FOREIGN PATENT DOCUMENTS

| | | |
|---|---|---|
| CN | 2899835 Y | 5/2007 |
| EP | 0377695 A1 | 7/1990 |
| EP | 1060728 A1 | 12/2000 |
| EP | 1172113 A1 | 1/2002 |
| JP | 2001259047 A | 9/2001 |
| JP | 521940 | 1/2005 |
| WO | WO-8911701 A1 | 11/1989 |
| WO | WO-9100730 A1 | 1/1991 |
| WO | WO-9322277 A1 | 11/1993 |
| WO | WO-9506411 A1 | 3/1995 |
| WO | WO-9814200 A1 | 4/1998 |
| WO | WO-9845313 A1 | 10/1998 |
| WO | WO-9856397 A1 | 12/1998 |
| WO | WO-9900123 A1 | 1/1999 |
| WO | WO-01/55109 | 8/2001 |
| WO | WO-0170337 A1 | 9/2001 |
| WO | WO-0170708 A1 | 9/2001 |
| WO | WO-0212887 A2 | 2/2002 |
| WO | WO-0215909 A1 | 2/2002 |
| WO | WO-0218327 A2 | 3/2002 |
| WO | WO-02059095 A1 | 8/2002 |
| WO | WO-02059107 A1 | 8/2002 |
| WO | WO-02059108 A1 | 8/2002 |
| WO | WO-02059117 A1 | 8/2002 |
| WO | WO-02067869 A2 | 9/2002 |
| WO | WO-02068387 A2 | 9/2002 |
| WO | WO-02068388 A2 | 9/2002 |
| WO | WO-02081443 A1 | 10/2002 |
| WO | WO-02085925 A2 | 10/2002 |
| WO | WO-03006620 A2 | 1/2003 |
| WO | WO-03007949 A1 | 1/2003 |
| WO | WO-03009847 A1 | 2/2003 |
| WO | WO-03009850 A1 | 2/2003 |
| WO | WO-03026576 A2 | 4/2003 |
| WO | WO-2004078716 A1 | 9/2004 |
| WO | WO-2004078717 A1 | 9/2004 |
| WO | WO-2004087159 A1 | 10/2004 |
| WO | WO-2005033254 A1 | 4/2005 |
| WO | WO-2005040109 A1 | 5/2005 |
| WO | WO-2005047251 A1 | 5/2005 |
| WO | WO-2005077935 A1 | 8/2005 |
| WO | WO-2006019787 A2 | 2/2006 |
| WO | WO-2006020277 A2 | 2/2006 |
| WO | WO-2006072393 A2 | 7/2006 |
| WO | WO-2007015157 A2 | 2/2007 |
| WO | WO-2007015162 A1 | 2/2007 |
| WO | WO-2007041052 A2 | 4/2007 |
| WO | WO-2007041061 A2 | 4/2007 |
| WO | WO-2007047496 A2 | 4/2007 |
| WO | 2008063330 A2 | 5/2008 |
| WO | 2008087190 A2 | 7/2008 |
| WO | 2009008991 A2 | 1/2009 |
| WO | 2009067501 A2 | 5/2009 |
| WO | 2009097542 A2 | 8/2009 |
| WO | 2009117415 A2 | 9/2009 |

OTHER PUBLICATIONS

Johnstone, B. et al., "In vitro chondrogenesis of bone marrow-derived mesenchymal progenitor cells," Exp Cell Res (1998) 238(1): 265-272.

Kafri, T. et al., "A packaging cell line for lentivirus vectors," J. Virol. (1999) 73: 576-584.

Klein, T.M. et al., "High-velocity microprojectiles for delivering nucleic acids into living cells," Nature, vol. 327:70-73 (1987).

Ladner, M.B. et al., "Human CSF-1: gene structure and alternative splicing of mRNA precursors," (1987) EMBO J. 6: 2693-2698.

Lever et al., "Demonstration of a Catecholaminergic Innervation in Human Perirenal Brown Adipose Tissue at Various Ages in the Adult," Anat Rec. Jul. 1986, 215(3): 251-5, 227-9.

Lin et al. 2002. "Spatially discrete, light driven protein expression." Chemistry & Biology, vol. 9, 1347-53.

Makino, S. et al., "Cardiomyocytes can be generated from marrow stromal cells in vitro," J. Clin. Invest. (1999) 103(5): 697-705.

Mannino, R.J. et al., "Liposome mediated gene transfer," (1988) BioTechniques 6:682-690.

Masamoto et al., "Intragastric Administration of TRPV1, TRPV3, TRPM8, and TRPA1 Agonists Modulates Autonomic Thermoregulation in Different Manners in Mice," Bioscience, Biotechnology, and Biochemistry. vol. 73 (2009), No. 5 pp. 1021-7.

Mayer, G. et al., "Biologically Active Molecules with a 'Light Switch'," Angew. Chem. Int. Ed. 45, 4900—4921 (2006).

McKnight, S.L. et al., "The distal transcription signals of the herpesvirus tk gene share a common hexanucleotide control sequence," (1984) Cell 37: 253-262.

McMinn, J.E. et al., "Neuroendocrine mechanisms regulating food intake and body weight," Obesity Reviews, vol. 1 (1):37-46 (2000).

Minokoshi et al., "Sympathetic Activation of Lipid Synthesis in Brown Adipose Tissue in the Rat," J. Pvsio. (1988) 398, 361-70.

Mochizuki, H. et al., "High-titer human immunodeficiency virus type 1-based vector systems for gene delivery into nondividing cells," J. Virol. (1998) 72: 8873-8883.

Molecular Biology of the Cell, 3rd Edition, ed. By Alberts et al., New York: Garland Publishing, 1994, Ch. 19.

National Institute of Health, Clinical Guidelines on the Identification, Evaluation, and Treatment of Overweight and Obesity in Adults (1998).

Ng, S.Y. et al., "Evolution of the functional human beta-actin gene and its multi-pseudogene family: conservation of noncoding regions and chromosomal dispersion of pseudogenes," (1985) Mol. Cell Biol. 5: 2720-2732.

Palucki, B.L. et al., "Discovery of (2S)-N-[(1R)-2-[4-cyclohexyl-4-[[(1,1-dimethylethyl)amino]carbonyl]-1-piperidinyl]-1- [(4-fluorophenyl)methyl]-2-oxoethyl]-4-methyl-2-piperazinecarboxamide (MB243), a potent and selective melanocortin subtype-4 receptor agonist," Bioorg Med Chem Lett. Jan. 3, 2005;15(1):171-175.

Rehnmark, S. et al., "Alpha- and beta-adrenergic induction of the expression of the uncoupling protein thermogenin in brown adipocytes differentiated in culture," J Biol Chem 265: 16464-16471, 1990.

Reiman et al., "Characterization and Functional Role of Coltage Gated Cation Conductances in the Glucagon-Like Peptide-1 Secreting GLUTag cell line," J Physiol, 2005, 161-175.

Rial et al., "The Structure and Function of the Brown Fat Uncoupling Protein UCP1: Current Status," Biofactors 8 p. 209-219 (1998).

Ricquier et al., "Contribution to the Identification and Analysis of the Mitochondrial Uncoupling Proteins," Journal of Bioenergetics and Biomembranes vol. 31, No. 5 (Oct. 1999) 407-418.

Rosell et al., "Skin Impedance From 1 Hz to 1MHz," IEEE Transactions on Biomedical Engineering, vol. 35, No. 8, Aug. 1988, 649-651.

Rosenfeld, M.A. et al., "Adenovirus-mediated transfer of a recombinant alpha 1-antitrypsin gene to the lung epithelium in vivo," (1991) Science 252:431-434.

Rosenfeld, M.A. et al., "In vivo transfer of the human cystic fibrosis transmembrane conductance regulator gene to the airway epithelium," (1992) Cell 68:143-155.

Rothwell, Nancy J. et al., "A Role for Brown Adipose Tissue in Diet-Induced Thermogenesis," Nature, vol. 281:31-35 (1979).

Saito et al. 2009. "High Incidence of Metabolically Active Brown Adipose Tissue in Healthy Adult Humans: Effects of Cold Exposure and Adiposity." Diabetes. 58, 1526-31.

(56) References Cited

OTHER PUBLICATIONS

Salmons, B. And Gunzburg, W. H., "Targeting of Retroviral Vectors for Gene Therapy," Hum. Gene Therapy (1993) 4: 129-141.
Sambrook et al. (1989) Molecular Cloning, a laboratory manual, Cold Spring Harbor Laboratories, N. Y.
Schmelz et al., "Delayed responses to electrical stimuli reflect C-fiber responsiveness in human microneurography," Exp Brain Res, 1995, 104: 331-336.
Sebhat, I.K. et al., "Design and pharmacology of N-[(3R)-1,2,3,4-tetrahydroisoquinolinium- 3-ylcarbonyl]-(1R)-1-(4-chlorobenzyl)-2-[4-cyclohexyl-4-(1H-1,2,4-triazol- 1-ylmethyl)piperidin-1-yl]-2-oxoethylamine (1), a potent, selective, melanocortin subtype-4 receptor agonist," J Med Chem. Oct. 10, 2002;45(21):4589-93.
Seydoux et al., "Impaired Metabolic Response to Nerve Stimulation in Brown Adipose Tissue of Hypothyroid Rats," Molecular and Cellular Endocrinology 25 p. 213-226 (1982).
Shigekawa, K. et al., "Electroporation of eukaryotes and prokaryotes: a general approach to the introduction of macromolecules into cells," (1988) BioTechniques 6:742-751.
Shimizu et al., "Sympathetic Activation of Glucose Utilization in Brown Adipose Tissue in Rats," Journal of Biochemistry, vol. 110, No. 5, 1991, pp. 688-692.
Solicore Flexion Batteries Product Line, available at Solicore, Inc. website, date of first publication unknown, revision 3 date Jan. 2007 (1 page).
Solicore SF-2529 Product Brochure, date of first publication unknown, revision 2 date Aug. 2008 (3 pages).
Solicore SF-4823 Product Brochure, date of first publication unknown, revision 2 date Aug. 2008 (3 pages).
Stylopoulos et al., "Roux-en-Y Gastric Bypass Enhances Energy Expenditure and Extends Lifespan in Diet-Induced Obese Rats," Obesity 17 (Oct. 1, 2009), 1839-47.
Sustained and Controlled Release Drug Delivery Systems, J.R. Robinson, ed., Marcel Dekker, Inc., New York, 1978.
Sutton, R.E. et al., "Human immunodeficiency virus type 1 vectors efficiently transduce human hematopoietic stem cells," J. Virol. (1998) 72: 5781-5788.
Tajino K, et al, "Application of Menthol to the Skin of Whole Trunk in Mice Induces Autonomic and Behavioral Heat-Gain Responses," Am J Physiol Regul Integr Comp Physiol. Nov. 2007; 293(5):R2128-35, Epub Aug. 29, 2007.
Testerman et al. 2006. "Electrical Stimulation as Therapy for Neurological Disorders: The basics of Implantable Neurological Stimulators." IEEE Engineering in Medicine and Biology Magazine. Sep./Oct., 74-8.
Toii et al. "Fall in Skin Temperature of Exercising Man." Br. J. Sp. Med. 26.1(1992):29-32.
van Marken Lichtenbelt et al, "Cold Activated Brown Adipose Tissue in Healthy Men," N. Engl. J. Med., Apr. 2009, 360, 1500 1508.
Virtanen, Kirsi A. et al., "Functional Brown Adipose Tissue in Healthy Adults," The New England Journal of Medicine, vol. 360:1518-1525 (2009).
Wagner, E. et al., "Coupling of adenovirus to transferrin-polylysine/DNA complexes greatly enhances receptor-mediated gene delivery and expression of transfected genes," Proc. Natl. Acad. Sci. USA (1992)89: 6099-6103.
Weidner et al., "Time course of post-excitatory effects separates afferent human C fibre classes," J Physiol, 2000, 527: 185-191.
Wells, J. et al., "Application of infrared light for in vivo neural stimulation," J Biomed Opt. Nov.-Dec. 2005;10(6):064003.
Wells, J. et al., "Biophysical mechanisms of transient optical stimulation of peripheral nerve," Biophys J. Oct. 1, 2007;93(7):2567-80. Epub May 25, 2007.
Wells, J. et al., "Optical stimulation of neural tissue in vivo," Opt Lett. Mar 1, 2005;30(5):504-6.
Wells, J. et al., "Pulsed laser versus electrical energy for peripheral nerve stimulation," J Neurosci Methods. Jul. 30, 2007;163(2):326-37. Epub Mar. 31, 2007.
Wells, J. et al., "Optically mediated nerve stimulation: Identification of injury thresholds.," Lasers Surg Med. Jul. 2007;39(6):513-26.
Wold, W., Adenovirus Methods and Protocols, Humana Methods in Molecular Medicine (1998), Blackwell Science, Ltd.
Wu et al., "A pilot study to evaluate the effect of splanchnic nerve stimulation on body composition and food intake in rats," Obes Surg, 2009, 19:1581-1585.
Xiong, C. et al., "Sindbis virus: an efficient, broad host range vector for gene expression in animal cells," Science (1989) 243: 1188-1191.
Xu, L. et al., "CMV-beta-actin promoter directs higher expression from an adeno-associated viral vector in the liver than the cytomegalovirus or elongation factor 1 alpha promoter and results in therapeutic levels of human factor X in mice," (2001) Hum Gene Ther. 12:563-73.
Ye, Zhixiong et al., "Discovery and activity of (1R,4S,6R)-N-[(1R)-2-[4-cyclohexyl-4-[[(1,1-dimethylethyl)amino]carbonyl]-1-[(4-fluorophenyl)methyl]-2-oxoethyl]-2-methyl-2-azabicyclo[2.2.2]octane-6-carboxamide (3,RY764), a potent and selective melanocortin sybtype-4 receptor agonist," Bioorganic & Medicinal Letters, vol. 15(15):3501-3505 (2005).
Yin et al., "Inhibitory Effects of Intestinal Electrical Stimulation on Food Intake, Weight Loss, and Gastric Emptying in Rats," Am J Physiol Regul Integr Comp Physiiol, 2007, R78-82.
Yoo, Y.U. et al., "The chondrogenic potential of human bone-marrow-derived mesenchymal progenitor cells," J. Bone Joint Surg. Am. (1998) 80(12): 1745-1757.
Zhao, H. et al "A novel promoter controls Cyp19a1 gene expression in mouse adipose tissue," (2009) Reproduct. Biol. Endrocrin. 7: 37-45.
Zheng et al., "Stimulation of sympathetic innervations in the upper gastrointestinal tract as a treatment for obesity," Med Hyp, 2009, 72: 706-710.
Australian Office Action for Application No. 2010343059, issued Aug. 30, 2013. (5 pages).
International Preliminary Report on Patentability mailed Aug. 2, 2012 for Application No. PCT/US2010/062464 (6 pages) .
International Search Report and Written Opinion for PCT/US 10/62464 dated Feb. 24, 2011 (8 pages).
Office action issued in Chinese Application No. 201080065678.8 dated Mar. 21, 2014. (Chinese original and English translation).
"Shining a light on disease—tracking light-emitting bacteria during infection," Society for General Microbiology, Sep. 9, 2009 (1 page).
3m CoTrain™ 9702 Membrane Brochure 2009 (2 pages).
3m CoTrain™ 9705 Membrane Brochure 2009 (2 pages).
3m CoTrain™ 9706 Membrane Brochure 2009 (2 pages).
3m CoTrain™ 9707 Membrane Brochure 2009 (2 pages).
3m CoTrain™ 9712 Membrane Brochure 2009 (2 pages).
3m CoTrain™ 9715 Membrane Brochure 2009 (2 pages).
3m CoTrain™ 9716 Membrane Brochure 2009 (2 pages).
3m CoTrain™ 9728 Membrane Brochure 2009 (2 pages).
3m CoTrain™ Membranes copyright 2010 at 3M website.
Accornero et al 'Selective Activation of peripheral nerve fibre groups of different diameter by triangular shaped stimulus pulses' J. Physiol (1977) 273 pp. 539-560.
Australian Office Action for Application No. 1010343059, issued Aug. 30, 2013 (5pages).
Bakshi RK et al Bioorg Med Chem Lett Jul. 15, 2005: 15(4) pp. 3430-3433.
Bartlet et al 'Brown adipose tissue activity controls triglyceride clearance' Nature Medicine, V. 17, No. 2 Feb. 2011 pp. 200-206.
Berkner et al (1998) BioTechniques 6: 616.
Bing, C. et al 'Hyperphagia in cold-exposed rats is accompanied by decreased plasma leptin but unchaged hypothalmic NPY' Am J Physiol Regulartory Integrative Compay Physiol 274: 62-68, 1998.
Birks, R.I., "Regulation by patterned preganglionic neural activity of transmitter stores in a sympathetic ganglion," J Physiol, 1978, 280: 559-572.
Boshart et al (1985) Cell 41: 521-530.
Bostock et al 'Velocity recovery cycles of C fibres innervating human skin' J Physiol 2003 553.2 pp. 649-663.
Bouillaud et al 'Increased Level of mRNA for the Uncoupling Protein in Brown Adipose Tissue of Rats during Thermogenesis

(56) References Cited

OTHER PUBLICATIONS

Induced by Cold Exposure or Norepinephrine Infusion' The Journal of Biological Chemistry V 259 No. 18 pp. 11583-11586 (1984).
Bredenbeek, P.J. et al J. Virol (1993) 67-6439-6446.
Bugajksi A.J. et al 'Effect of long-term vagal stimulation on food intake and body weight during diet induced obesity in rats' J Phys Pharm 58 (suppl 1) 5-12.
Cannon, et al 'Brown Adipose Tissue: Function and Physiological Signifcane' Physiol Rev 2004 84 pp. 277-359.
Cannon, et al 'Nonshivering Thermogenesis and its Adequate Measurerment in Metabolic Studies' J. Exp. Biol. 214 (2011) pp. 242-253.
Capecchi (1980) cell 22: 479-488.
Cassiede P., et al J. Bone Miner Res (1996) 11(9) pp. 1264-1273.
Cheneval et al (1991) Proc Natl Acad Sci USA 88: 8465-9.
Chu et al (1981) Gene 13: 197.
Clark et al J. Drug Target 7, 269-83 (1999).
Collins, SI 'The cervial sympathetic nerves in surgery of the neck' Otolaryngol Head Neck Surg 1991 105: 544.
Crago et al., "The choice of pulse duration for chronic electrical stimulation via surface, nerve, and intramuscular electrodes," Ann Biomed Eng, 1974, 2: 252-264.
Current Protocols in Molecular Biology, Ausubel et al. (eds.) Greene Publishing Associates, (1989), Sections 9.10-9.14.
Davidson, B.L. et al Nature Genetics (1993) 3: 219-223.
Davis et al. (1986) Basic Methods in Molecular Biology, Elsevier.
Douglas, J. et al Nature Biotech (1999) 17: 470-475.
Drazen, D.L. Woods, S.C. Curr. Opin Nutr Metab Care 2003 6: 621-629.
Dull et al J Virol (1998) 72 8463-8471.
Ekblom, et al Ann N.Y. Acad Sci 857: 194-211 (1998).
Enerback 'The origins of Brown Adipose Tissue' New Eng. J. Med 360 19(2009) pp. 2021-2023.
Felgner et al (1987) Proc Natl Acad Sci USA 84: 7413-7417.
Flaim et al (1976) 'Functional and Anatomical Characteristics of the Nerve-Brown Adipose Interation in the rat' Pflugers Arch 365, 9-14.
Foster et al 'Heterogeneity of the Symathetic Innervation of Rat Interscapular Brown Adipose Tissue via Intercoastal Nerves' Can J. Physiol Pharmacol Jun. 1982 60(6) pp. 747-754.
Freeman, P et al 'Brown Adipose Tissue Thermogensis Induced by Low Level Electrical Stimulation of Hypothalamus in rats' Brain Research Bulletin (1987) vol. 18 pp. 7-11.
Frolov, I et al Proc Natl Acad Sci USA (1996) 93: 11371-11377.
Fruhbeck et al 'BAT: A New Target for Human Obesity?' Trends Pharamcol Sci 30.8 (2000() pp. 387-396.
Graham et al (1973) Virol 52 pp. 456-467.
Gronthos S Blood (1994) 84(12) pp. 4164-4173.
Heaton 'The Distribution of Brown Adipose Tissue in the Human' J. Anat 1972 112 (Pt 1) pp. 35-39.
Herlitze, S. Curr Opin Neurobiol (2007) 17(1) pp. 87-94 Epub Dec. 15, 2006 Review.
Herpin T.F. et al J Med Chem Mar. 27, 2003 46(7) pp. 1123-1126.
Hodgkin & Huxley, "A quantitative description of membrane current and its application to conduction and excitation in nerve," J Physiol, 1952, 117:500-544.
Horwitz, et al 'Noerpinephrine-induced depolarization of brown fat cells' Proc N.A.A. 1969, 64 pp. 113-120.
International Preliminary Report on Patentability mailed Aug. 2, 2012 for Application No. PCT/US2010/062464 (6 pages).
International Search Report and Written Opinion for PCT/US10/62464 dated Feb. 24, 2011 (8 pages).
McKnight, S.L. 1984 Cell 37 253-262.
Morrison, S.F. RVLM and raphe differentially regulate sympathetic outflows to splanchnic and brown adipose tissue, American Journal of Physiology—Regulatory, Integrative and Comparative Physiology, published Apr. 1, 1999, vol. 276 No. 4 pp. 962-973.
Office action issued in Japanese Application No. 2012-550003 dated Sep. 16, 2014. (Japanese original and English translation).
Rosenfeld (1992) Cell 68 pp. 143-155.
U.S. Appl. No. 12/605,409, filed Oct. 26, 2009.
U.S. Appl. No. 12/976,648, filed Dec. 22, 2010.
U.S. Appl. No. 12/980,635, filed Dec. 29, 2010.
U.S. Appl. No. 12/980,695, filed Dec. 29, 2010.
U.S. Appl. No. 12/980,710, filed Dec. 29, 2010.
U.S. Appl. No. 13/977,501, filed Oct. 2, 2013.
U.S. Appl. No. 13/977,543, filed Jun. 28, 2013.
U.S. Appl. No. 61/427,968, filed Dec. 29, 2010.
U.S. Appl. No. 61/427,991, filed Dec. 29, 2010.
U.S. Appl. No. 61/428,008, filed Dec. 29, 2010.
U.S. Appl. No. 61/428,013, filed Dec. 29, 2010.
Zheng et al 'Stimulation of sympathetic innervations in the upper gastrointestinal tract as a treatment for obesity' Med Hyp 2009 72 pp. 706-710.
Zhixiong Y et al Bioorg Med Chem Lett Jul. 15, 2005 (140 pp. 3501-3505.

\* cited by examiner

METHODS AND DEVICES FOR ACTIVATING BROWN ADIPOSE TISSUE USING ELECTRICAL ENERGY

CROSS REFERENCE TO RELATED APPLICATIONS

The present application is a continuation of U.S. application Ser. No. 12/980,659 filed Dec. 29, 2010 entitled "Methods And Devices For Activating Brown Adipose Tissue Using Electrical Energy," which claims priority to U.S. Provisional Application Ser. No. 61/297,405 filed Jan. 22, 2010 entitled "Methods And Devices For Activating Brown Adipose Tissue," which are hereby incorporated by reference in their entireties.

U.S. application Ser. No. 12/980,659 was concurrently filed on Dec. 29, 2010 with U.S. application Ser. No. 12/980,635 entitled "Diagnostic Methods And Combination Therapies Involving MC4R," which claims the priority of U.S. Provisional Application Ser. No. 61/297,483 entitled "Diagnostic Methods And Combination Therapies Involving MC4R," which are hereby incorporated by reference herein in their entireties.

FIELD OF THE INVENTION

The present invention relates to methods and devices for inducing weight loss, and in particular to methods and devices for activating brown adipose tissue using electrical energy.

BACKGROUND OF THE INVENTION

Obesity is becoming a growing concern, particularly in the United States, as the number of people with obesity continues to increase and more is learned about the negative health effects of obesity. Severe obesity, in which a person is 100 pounds or more over ideal body weight, in particular poses significant risks for severe health problems. Accordingly, a great deal of attention is being focused on treating obese patients.

Surgical procedures to treat severe obesity have included various forms of gastric and intestinal bypasses (stomach stapling), biliopancreatic diversion, adjustable gastric banding, vertical banded gastroplasty, gastric plications, and sleeve gastrectomies (removal of all or a portion of the stomach). Such surgical procedures have increasingly been performed laparoscopically. Reduced postoperative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body cavity wall. However, such surgical procedures risk a variety of complications during surgery, pose undesirable post-operative consequences such as pain and cosmetic scarring, and often require lengthy periods of patient recovery. Patients with obesity thus rarely seek or accept surgical intervention, with only about 1% of patients with obesity being surgically treated for this disorder. Furthermore, even if successfully performed and initial weight loss occurs, surgical intervention to treat obesity may not result in lasting weight loss, thereby indicating a patient's need for additional, different obesity treatment.

Nonsurgical procedures for treating obesity have also been developed. However, effective therapies for increasing energy expenditure and/or altering a patient's metabolism, e.g., a basal metabolic rate, leading to improvements in metabolic outcomes, e.g., weight loss, have focused on pharmaceutical approaches, which have various technical and physiological limitations.

It has been recognized in, for example, U.S. Pat. No. 6,645,229 filed Dec. 20, 2000 and entitled "Slimming Device," that brown adipose tissue (BAT) plays a role in the regulation of energy expenditure and that stimulating BAT can result in patient slimming. BAT activation is regulated by the sympathetic nervous system and other physiological, e.g., hormonal and metabolic, influences. When activated, BAT removes free fatty acids (FFA) and oxygen from the blood supply for the generation of heat. The oxidative phosphorylation cycle that occurs in the mitochondria of activated BAT is shown in FIGS. 1 and 2.

Accordingly, there is a need for improved methods and devices for treating obesity and in particular for activating BAT.

SUMMARY OF THE INVENTION

The present invention generally provides methods and devices for activating brown adipose tissue using electrical energy. In one embodiment, a medical method is provided that includes positioning a device in contact with tissue of a patient proximate to a depot of brown adipose tissue, and activating the device to deliver an electrical signal to the patient to activate the brown adipose tissue and increase energy expenditure of the brown adipose tissue. The electrical signal has a modulating signal and a carrier signal. The carrier signal can have any carrier frequency, such as a carrier frequency in a range of about 10 to 400 kHz, e.g., in a range of about 200 to 250 kHz. The modulating signal can have any activation frequency, such as an activation frequency in a range of about 0.1 to 100 Hz, e.g., less than about 10 Hz.

The electrical signal can have a variety of characteristics. For example, the electrical signal can have a pulse width in a range of about 10 μs to 10 ms, a voltage having an amplitude in a range of about 1 to 20 V, and/or a current having an amplitude in a range of about 2 to 6 mA. The electrical signal can be delivered to the patient continuously for a predetermined amount of time, e.g., at least four weeks. The device can be configured to be in continuous direct contact with the tissue of the patient for at least one day with the device generating the electrical signal and continuously delivering the electrical signal to the patient for at least one day.

The depot of brown adipose tissue can be located anywhere in the patient, such as in a supraclavicular region of the patient.

The device can have a variety of configurations. In some embodiments, the device can include a housing configured to be disposed in direct contact with the tissue of the patient proximate to the depot of brown adipose tissue, and a signal generator coupled to the housing and configured to generate the electrical signal and to deliver the electrical signal to the patient. The signal generator can be located within the housing. The housing can include a housing of a patch attached to the patient. The device can also include a controller configured to turn the signal generator on to start the signal generator generating the electrical signal, turn the signal generator off to stop the signal generator from generating the electrical signal, or both. The controller can be configured to be located remotely from the patient and to be in electronic communication with the signal generator, and/or the controller can be configured to be implanted entirely within the patient.

The device can be positioned in contact with tissue of a patient in a variety of ways. For example, the device can be positioned in contact with tissue of a patient by transcutaneously applying the device to an exterior skin surface of the patient. For another example, the device can be positioned in contact with tissue of a patient by subcutaneously positioning at least a portion of the device within the patient. In some embodiments, the device can be implanted entirely within the patient. For still another example, the device can be positioned proximate to at least one of a supraclavicular region, a nape of a neck, a scapula, a spinal cord, proximal branches of the sympathetic nervous system that terminate in BAT depots, and a kidney.

The medical method can also include removing the device from the patient, repositioning the device in contact with tissue of the patient proximate to another depot of brown adipose tissue, and activating the device to deliver another electrical signal to the patient to activate the other depot of brown adipose tissue and increase energy expenditure of the other depot of brown adipose tissue. The depot of brown adipose tissue can be in a supraclavicular region on one of a left and right side of a sagittal plane of the patient, and the other depot of brown adipose tissue can be in a supraclavicular region on the other of the left and right side of the sagittal plane of the patient. The device can be removed and repositioned at any time, such as after the electrical signal has been delivered to the depot of brown adipose tissue for a threshold amount of time, e.g., at least seven days. The device can continuously deliver the electrical signal to the patient during the threshold amount of time. In some embodiments, in response to a trigger event, the device can be removed from contact with tissue of the patient and repositioned to be in contact with another area of tissue of the patient proximate to another depot of brown adipose tissue. The trigger event can include at least one of the patient eating, the patient resting, a threshold temperature of the patient, a directional orientation of the patient, a change in the patient's weight, a change in the patient's tissue impedance, manual activation by the patient or other human, a blood chemistry change in the patient, and a signal from a controller in electronic communication with the device.

In some embodiments, the method can include stopping application of the electrical signal, waiting a predetermined amount of time, and activating the device to deliver another electrical signal to the patient to activate the depot of brown adipose tissue and increase energy expenditure of the brown adipose tissue. The stopping, the waiting, and the activating can be repeated until occurrence of a threshold event. The threshold event can include, for example, at least one of a predetermined amount of time and a predetermined physiological effect.

The device can be activated to deliver an electrical signal to the patient to activate the brown adipose tissue without cooling the patient or the brown adipose tissue and/or without any pharmaceutical administered to the patient to activate the brown adipose tissue.

The method can optionally include positioning a second device in contact with tissue of the patient proximate to another depot of brown adipose tissue, and activating the second device to deliver a second electrical signal to the patient to activate the other depot of brown adipose tissue and increase energy expenditure of the other depot of brown adipose tissue. The second device can deliver the second electrical signal to the patient simultaneously with the device delivering the electrical signal to the patient.

The method can have any number of variations. For example, the method can include reducing power of the electrical signal until a first predetermined threshold event occurs, and subsequently increasing the power of the electrical signal until a second predetermined threshold event occurs. For another example, the device can be activated in response to a trigger event including at least one of the patient eating, the patient resting, a threshold temperature of the patient, a directional orientation of the patient, a change in the patient's weight, a change in the patient's tissue impedance, manual activation by the patient or other human, a blood chemistry change in the patient, and a signal from a controller in electronic communication with the device. For still another example, the method can include imaging the patient to locate the depot of brown adipose tissue prior to positioning the device in contact with tissue of the patient proximate to the depot of brown adipose tissue.

In another embodiment, a medical method is provided that includes positioning a device in contact with tissue of a patient proximate to a first depot of brown adipose tissue, activating the device to deliver a first electrical signal to the patient to activate the first depot and increase energy expenditure of the first depot, delivering the first electrical signal to the patient until a first threshold event occurs, when the first threshold event occurs, stopping delivery of the first electrical signal to the patient, delivering a second electrical signal to the patient to activate a second depot of brown adipose tissue and increase energy expenditure of the second depot, delivering the second electrical signal to the patient until a second threshold event occurs, and when the second threshold event occurs, stopping delivery of the second electrical signal.

The first and second electrical signals can have a variety of characteristics. For example, each of the first and second electrical signals can have a modulating signal and a carrier signal. The modulating signal can have an activation frequency in a range of about 0.1 to 100 Hertz, and the carrier signal can have a carrier frequency in a range of about 10 to 400 kHz. For another example, the first and second electrical signals can be simultaneously delivered to the patient. For still another example, the first and second electrical signals can be sequentially delivered to the patient such that the patient receives only one of the first and second electrical signals at a time. When the second threshold event occurs, the device in contact with tissue of the patient proximate to the first depot can be activated to deliver a third electrical signal to the patient to activate the first depot and increase energy expenditure of the first depot.

The first and second threshold events can vary, and they can be the same as or different from one another. In some embodiments, the first threshold event can include passage of a first predetermined amount of time, and the second threshold event can include passage of a second predetermined amount of time. The first and second predetermined amounts of time can also vary, and they can also be the same as or different from one another. For example, the first and second predetermined amounts of time can each be at least about 24 hours, e.g., can each be at least about seven days.

The first and second depots of brown adipose tissue can be located anywhere in the patient, such as the first depot being located on one of a left and right side of a sagittal plane of the patient, and the second depot being located on the other of the left and right sides of the sagittal plane of the patient.

The method can vary in any number of ways. For example, before delivering the second electrical signal to the patient, the device can be repositioned to be in contact with tissue of the patient proximate to the second depot and using the device to deliver the second electrical signal to the patient. For another example, a second device can be positioned in contact with tissue of the patient proximate to the second depot, and the second device can be used to deliver the second electrical signal to the patient.

In another aspect, a medical device is provided including a housing configured to be disposed in direct contact with a body of a patient proximate to brown adipose tissue, and a signal generator located within the housing and configured to generate an electrical signal and to deliver the electrical signal to the body of the patient to electrically stimulate the brown adipose tissue. The electrical signal can have a variety of configurations, e.g., have a voltage having an amplitude of up to about 20 V, have an activation frequency in a range of about 5 to 10 Hz, and have a carrier frequency in a range of about 200 to 250 kHz.

The housing, e.g., a housing of a patch attached to the patient, can have a variety of sizes, shapes, and configurations. The housing can be configured to be applied to an exterior skin surface of the patient to transcutaneously deliver the electrical signal, e.g., using an electrode in direct contact with the exterior skin surface. In another embodiment, the housing can be configured to be at least partially implanted within the patient, e.g., implanted entirely within the patient, to subcutaneously apply the electrical signal to the patient. The housing can be configured to be in continuous direct contact with the body of the patient for at least one day with the signal generator generating the electrical signal and delivering the electrical signal to the body of the patient.

In some embodiments the medical device can also include a controller configured to turn the signal generator on to start the signal generator generating the electrical signal and/or turn the signal generator off to stop the signal generator from generating the electrical signal. The controller can be configured to be located remotely from the patient and to be in electronic communication with the signal generator. The controller can be configured to be implanted entirely within the patient.

In another aspect, a medical method is provided that includes positioning a device in contact with tissue of a patient proximate to a depot of brown adipose tissue, and activating the device to deliver an electrical signal to the patient to activate the brown adipose tissue, e.g., through sympathetic nerve stimulation and/or stimulating brown adipocytes directly, and increase energy expenditure of the brown adipose tissue. Positioning the device in contact with tissue of the patient can include transcutaneously applying the device to an exterior skin surface of the patient or subcutaneously positioning the device within the patient. In some embodiments, the patient can be imaged to locate the depot of brown adipose tissue prior to positioning the device in contact with tissue of the patient. The device can be positioned proximate to at least one of a nape of a neck, a scapula, a spinal cord, proximal branches of the sympathetic nervous system that terminate in BAT depots, and a kidney. In some embodiments, positioning a device in contact with tissue of a patient proximate to a depot of brown adipose tissue can include positioning the device proximate to a nerve that when depolarized, leads to the activation of the brown adipose tissue. The electrical signal can have a variety of configurations, e.g., have a voltage having an amplitude of about 20 Volts, have an activation signal pulse frequency in a range of about 5 to 10 Hertz, and have a carrier frequency in a range of about 200 to 250 kHz.

The method can vary in any number of ways. For example, the device can be activated in response to a trigger event including at least one of the patient eating, the patient resting, a threshold temperature of the patient, a directional orientation of the patient, a change in the patient's weight, a change in the patient's tissue impedance, manual activation by the patient or other human, a blood chemistry change in the patient, and a signal from a controller in electronic communication with the device. For another example, the device can be activated to deliver an electrical signal to the patient to activate the brown adipose tissue without cooling the patient or the brown adipose tissue and/or without any pharmaceutical administered to the patient to activate the brown adipose tissue. For yet another example, the electrical signal can be continuously delivered to the patient for a predetermined amount of time, e.g., at least four weeks. For another example, the method can include stopping application of the electrical signal, waiting a predetermined amount of time, and activating the device to deliver another electrical signal to the patient to activate the depot of brown adipose tissue and increase energy expenditure of the brown adipose tissue. The stopping, the waiting, and the activating can be repeated until occurrence of a threshold event, e.g., at least one of a predetermined amount of time and a predetermined physiological effect such as a predetermined amount of weight lost by the patient. For another example, the method can include reducing the power of the electrical signal until a first predetermined threshold event occurs (e.g., until a first predetermined period of time passes), and subsequently increasing the power of the electrical signal until a second predetermined threshold event occurs (e.g., until a second predetermined period of time passes, which can be the same or different from the first predetermined period of time). For yet another example, a second device can be positioned in contact with tissue of the patient proximate to another depot of brown adipose tissue, and the second device can be activated to deliver a second electrical signal to the patient to activate the other depot of brown adipose tissue and increase energy expenditure of the other depot of brown adipose tissue. The second device can deliver the second electrical signal to the patient simultaneously with the device delivering the electrical signal to the patient.

In some embodiments, the method can also include removing the device from the patient, repositioning the device in contact with tissue of the patient proximate to another depot of brown adipose tissue, and activating the device to deliver another electrical signal to the patient to activate the other depot of brown adipose tissue, e.g., through sympathetic nerve stimulation and/or direct stimulation of brown adipocytes, and increase energy expenditure of the other depot of brown adipose tissue. The device can be removed and repositioned after the electrical signal has been delivered to the depot of brown adipose tissue for a threshold amount of time, e.g., at least seven days. Alternatively or in addition, the device can be removed and repositioned in response to a trigger event including at least one of the patient eating, the patient resting, a threshold temperature of the patient, a directional orientation of the patient, a change in the patient's weight, a change in the patient's tissue impedance, manual activation by the patient or other human, a blood chemistry change in the patient, and a signal from a controller in electronic communication with the device.

In another embodiment, a medical method is provided that includes positioning a device on a body of a patient, e.g., on skin of the patient, generating an electrical signal with the device, and targeting the electrical signal to stimulate a tissue that regulates energy expenditure within the patient. At least a portion of the electrical signal can be periodic. At least a portion of the device can be positioned subcutaneously within the patient.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
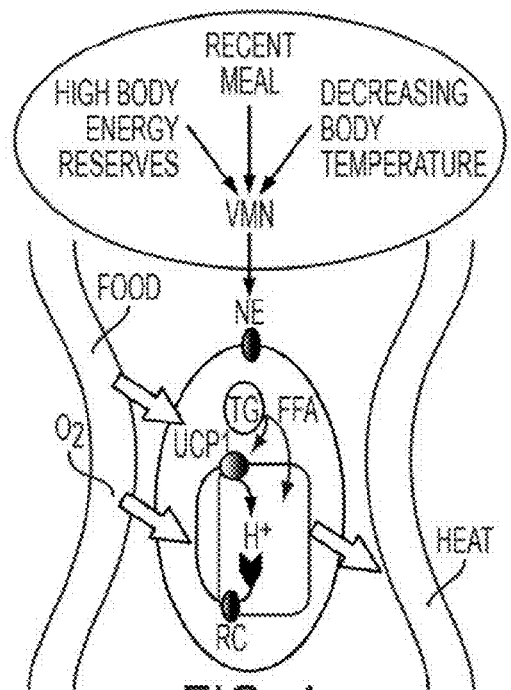
FIG. 1 is a schematic view of an oxidative phosphorylation cycle that occurs in mitochondria within BAT cells.
Figure 2:
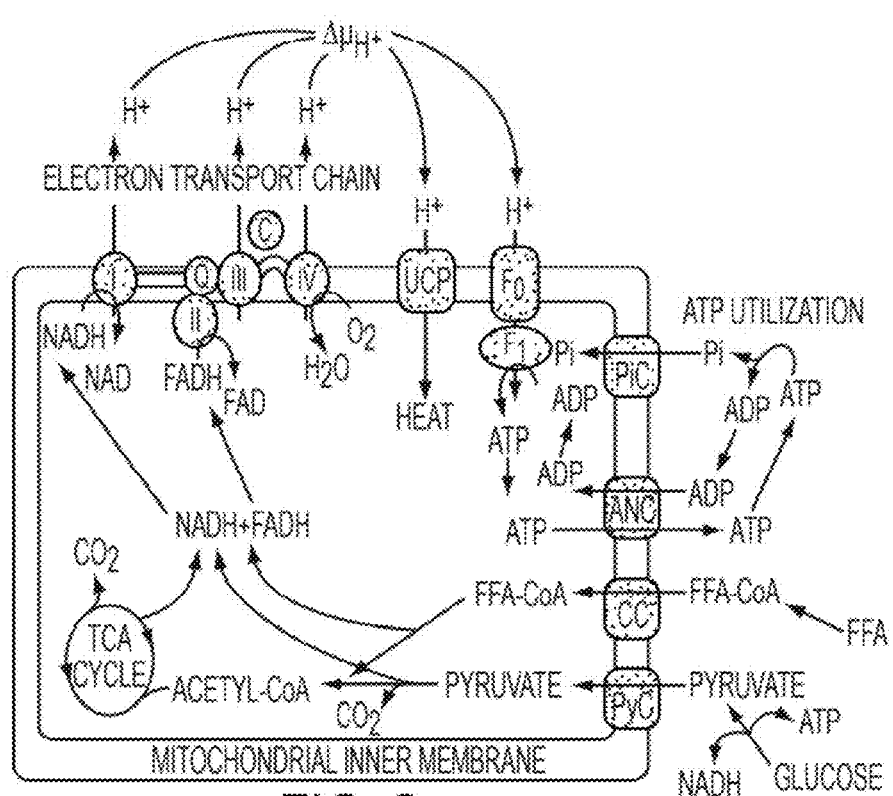
FIG. 2 is a schematic view of BAT mitochondria showing an oxidative phosphorylation cycle that occurs in the mitochondria.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for activating brown adipose tissue (BAT) using electrical energy. In general, the methods and devices can activate BAT to increase thermogenesis, e.g., increase heat production and energy expenditure in the patient, which over time can lead to one or more of weight loss, a change in the metabolism of the patient, e.g., increasing the patient's basal metabolic rate, and improvement of comorbidities associated with obesity, e.g., Type II diabetes, high blood pressure, etc. In an exemplary embodiment, a medical device is provided that activates BAT by electrically stimulating nerves that activate the BAT and/or electrically stimulating brown adipocytes directly, thereby increasing thermogenesis in the BAT and inducing weight loss through energy expenditure. In this way, weight loss can be induced without performing a major surgical procedure, without relying on administration of one or more pharmaceuticals, without relying on cooling of the patient, and without surgically altering a patient's stomach and/or other digestive organs.

Following a surgical procedure to treat obesity such as Roux-en-Y gastric bypass (RYGB), a patient can lose weight due to an increase in energy expenditure, as demonstrated in a rodent model for example in Stylopoulos et al., "Roux-en-Y Gastric Bypass Enhances Energy Expenditure And Extends Lifespan In Diet-Induced Obese Rats," *Obesity* 17 (1 Oct. 2009), 1839-47. Additional data from Stylopoulos et al. (not published in the previous article or elsewhere as of the filing date of the present non-provisional application) indicates that RYGB is also associated with increased levels of uncoupling protein 1 (UCP1), which is an uncoupling protein in mitochondria of BAT, as well as with a significant reduction in the size of fat stores within BAT and an increased volume of BAT. It thus appears that RYGB causes activation of BAT, although as discussed above, surgical procedures to treat obesity, such as gastric bypass, risk if not necessarily cause a variety of undesirable results. Devices and methods to activate BAT without a major surgical procedure like RYGB but instead with electrical nerve stimulation to increase energy expenditure are therefore provided.

One characteristic of BAT that distinguishes it from white adipose tissue (WAT) stores is the high number of mitochondria in a single BAT cell. This characteristic makes BAT an excellent resource for burning energy. Another distinguishing characteristic of BAT is that when activated, UCP1 is utilized to introduce inefficiency into the process of adenosine triphosphate (ATP) creation that results in heat generation. Upregulation of UCP1 is therefore a marker of BAT activation.

Activation of brown adipocytes leads to mobilization of fat stores within these cells themselves. It also increases transport of FFA into these cells from the extracellular space and bloodstream. FFAs in the blood are derived primarily from fats metabolized and released from adipocytes in WAT as well as from ingested fats. Stimulation of the sympathetic nervous system is a major means of physiologically activating BAT. Sympathetic nerve stimulation also induces lipolysis in WAT and release of FFA from WAT into the bloodstream to maintain FFA levels. In this way, sympathetic stimulation leads ultimately to the transfer of lipids from WAT to BAT followed by oxidation of these lipids as part of the heat generating capacity of BAT.

Figure 3:
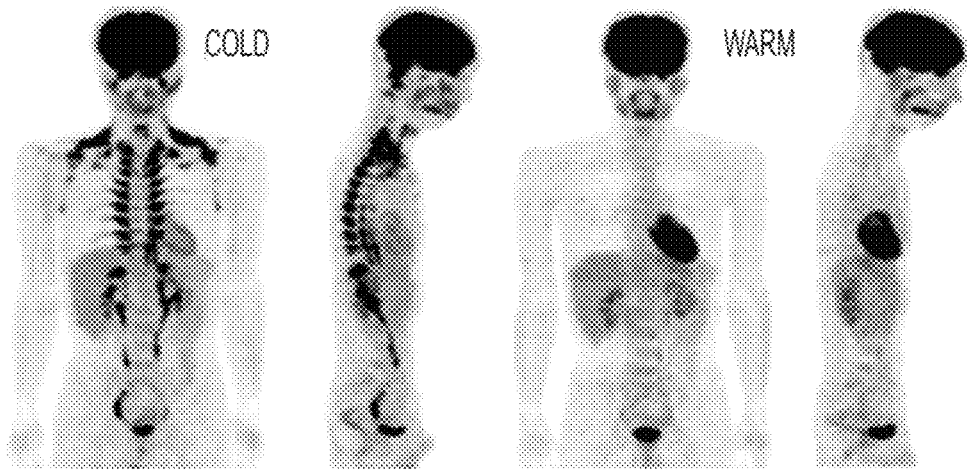
FIG. 3 is a schematic view of PET-CT images showing the locations of BAT depots in a patient subject to a cold environment and in the patient in a normal, warm environment.

The controlled activation of BAT can be optimized, leading to weight loss, by reducing the stores of triglycerides in WAT. A person skilled in the art will appreciate that exposure to cold temperature leads to the activation of BAT to help regulate body temperature. This knowledge allows the location of BAT to be readily assessed using positron emission tomography-computed tomography (PET-CT) imaging. FIG. 3 shows scans of a patient subjected to a cold environment (left two images) and the same patient scanned in a normal, warm environment (right two images). Shown in black are regions of intense glucose uptake—namely, the brain, the heart, the bladder, and in the cold environment, BAT. However these images show the locations of BAT depots—namely the nape of the neck, the supraclavicular region, over the scapula, alongside the spinal cord, and around the kidneys as referenced by, for example, Rothwell et al, "A Role For Brown Adipose Tissue In Diet-Induced Thermogenesis," *Nature*, Vol. 281, 6 Sep. 1979, and Virtanen et al., "Functional Brown Adipose Tissue in Healthy Adults," *The New England Journal of Medicine*, Vol. 360, No. 15, Apr. 9, 2009, 1518-1525.

A person skilled in the art will appreciate that adult humans have substantial BAT depots, as indicated, for example, in J. M. Heaton, "The Distribution Of Brown Adipose Tissue In The Human," *J Anat.*, 1972 May, 112(Pt 1): 35-39, and W. D. van Marken Lichtenbelt et al, "Cold-Activated Brown Adipose Tissue in Healthy Men," N. Engl. J. Med., 2009 April, 360, 1500-1508. A person skilled in the art will also appreciate that BAT is heavily innervated by the sympathetic nervous system, as indicated, for example, in Lever et al., "Demonstration Of A Catecholaminergic Innervation In Human Perirenal Brown Adipose Tissue At Various Ages In The Adult," *Anat Rec.*, 1986 July, 215(3): 251-5, 227-9. Further, "[t]he thin unmyelinated fibers that contain norepinephrine (and not NPY) are those that actually innervate the brown adipocytes themselves. They form a dense network within the tissue, being in contact with each brown adipocyte (bouton-en-passant), and their release of norepinephrine acutely stimulates heat production and chronically leads to brown adipose tissue recruitment". B. Cannon, and J. Nedergaard, "Brown Adipose Tissue: Function And Physiological Significance," *Physiol Rev.*, 2004: 84: 277-359.

Nerves innervating BAT can be stimulated to activate UCP1 and hence increase energy expenditure through heat dissipation through transcutaneous and/or direct stimulation of nerves innervating BAT. Transcutaneous and direct stimulation are each discussed below in more detail.

In some embodiments, transcutaneous and/or direct stimulation of nerves innervating BAT can be combined with one or more treatments, before and/or after transcutaneous and/or direct stimulation of BAT, which can help encourage BAT stimulation and/or increase an amount of BAT in a patient. For non-limiting example, a pharmaceutical can be administered to a patient, the patient can be cooled, the patient can be heated, a magnetic field can be targeted to a region of a patient, a BAT-stimulation procedure can be performed on the patient directed to a BAT depot and/or to a nerve innervating BAT, the patient can engage in weight loss therapies, and/or a surgical procedure can be performed on the patient, such as a procedure to induce weight loss and/or to improve metabolic function, e.g., glucose homeostatis, lipid metabolism, immune function, inflammation/anti-inflammatory balance, etc. A non-limiting example of cooling the patient includes applying a cold pack to skin of the patient for a period of time. The cold pack can be applied to a region of the skin with a high concentration of cold receptors, such as near the wrists, ankles, and/or regions having thermosensitive transient receptor potential (TRP) channels (e.g., TRPA1, TRPV1, TRPM8, etc.). Alternatively or in addition, the cold pack can be applied to the skin proximate to a BAT depot and/or to nerves innervating a BAT depot. Providing electrical stimulation, e.g., using an implanted electrical stimulation device, such that the BAT depot can be simultaneously activated through a mechanism associated with a lowered body temperature and electrically stimulated, thereby potentially further encouraging additive or synergistic activation of the BAT. Non-limiting examples of a nerve stimulation technique configured to stimulate a nerve innervating BAT include delivery of a medium to the nerve that induces an action potential in the nerve, e.g., electricity, light, mechanical manipulation or vibration, a magnetic field, a chemical substance, etc. Non-limiting examples of a BAT-stimulation procedure include inducing differentiation of muscle, WAT, preadipocytes, or other cells to BAT, and/or implanting or transplanting BAT cells into a patient. Non-limiting examples of implanting or transplanting BAT cells include removing cells from a patient, culturing the removed cells, and reimplanting the cultured cells; transplanting cells from another patient; implanting cells grown from embryonic stem cells, adult stem cells, or other sources; and genetically, pharmacologically, or physically altering cells to improve cell function. Non-limiting examples of such weight loss therapies include a prescribed diet and prescribed exercise. Non-limiting examples of such a surgical procedure include gastric bypass, biliopancreatic diversion, vertical sleeve gastrectomy, adjustable gastric banding, vertical banded gastroplasty, intragastric balloon therapy, gastric plication, Magenstrasse and Mill, small bowel transposition, biliary diversion, vagal nerve stimulation, duodenal endoluminal barrier, and procedures that allow for removal of food from the stomach. Combining one or more treatments, particularly a weight loss therapy or a weight loss surgical procedure which does not activate BAT, e.g., a procedure other than RYGB, biliopancreatic diversion (BPD) with or without duodenal switch, or some duodenal or other intestinal barrier (e.g., a prescribed diet and/or exercise program, adjustable gastric banding, vertical banded gastroplasty, sleeve gastrectomy, gastric plication, Magenstrasse and Mill, intragastric balloon therapy, some duodenal or other intestinal barrier, and small bowel transposition, with a means for acute or chronic activation of BAT such as the nerve stimulation discussed herein, can result in desirable patient outcomes through a combined approach.

Because BAT activation may lead to an increase in body temperature locally, regionally, or systemically, transcutaneous and/or direct stimulation of nerves innervating BAT can be combined with one or more heat dissipation treatments, before and/or after transcutaneous and/or direct stimulation of BAT. Non-limiting examples of such a heat dissipation treatment include inducing cutaneous/peripheral vasodilation, e.g., local or systemic administration of Alpha antagonists or blockers, direct thermal cooling, etc.

Figure 4:
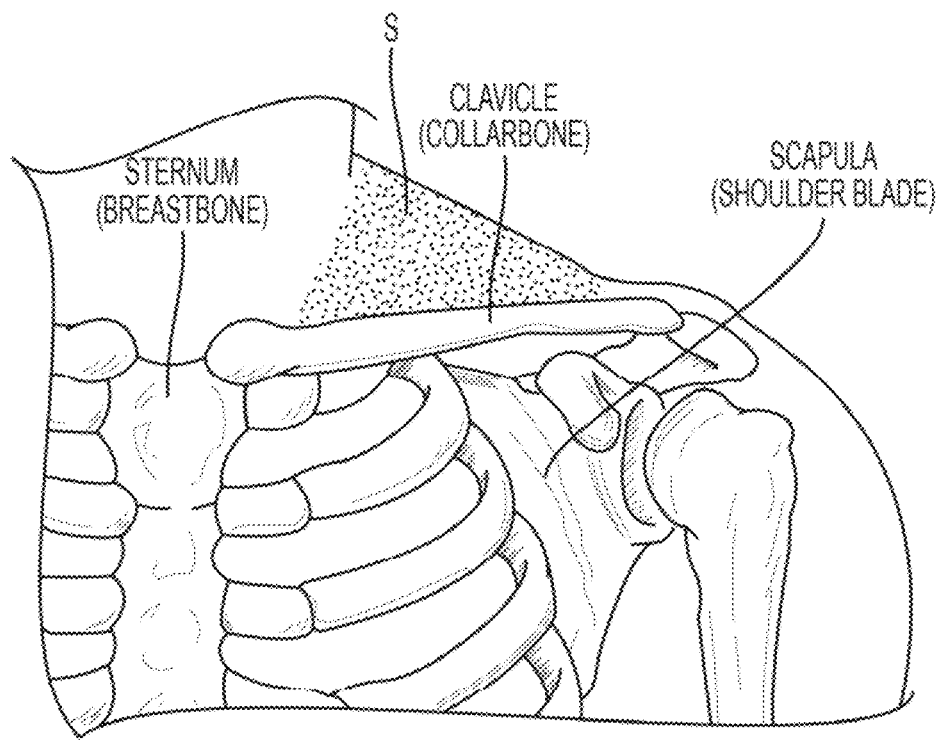
FIG. 4 is a transparent view of a portion of a human neck, chest, and shoulder area with a shaded supraclavicular region.

Whether BAT is activated directly and/or transcutaneously, target areas for BAT nerve stimulation and/or direct stimulation of brown adipocytes can include areas proximate to BAT depots, e.g., a supraclavicular region, the nape of the neck, over the scapula, alongside the spinal cord, near proximal branches of the sympathetic nervous system that terminate in BAT depots, and around at least one of the kidneys. Any BAT depot can be selected for activation. For non-limiting example, in one embodiment illustrated in FIG. 4, the device (not shown) can be positioned proximate to an area over a scapula in a supraclavicular region S. Identification of one or more BAT depots for activation can be determined on an individualized patient basis by locating BAT depots in a patient by imaging or scanning the patient using PET-CT imaging, tomography, thermography, or any other technique, as will be appreciated by a person skilled in the art. Non-radioactive based imaging techniques can be used to measure changes in blood flow associated with the activation of BAT within a depot. In one embodiment, a contrast media containing microbes can be used to locate BAT. The contrast media can be injected into a patient whose BAT has been activated. An energy sources such as low frequency ultrasound can be applied to the region of interest to cause destruction of bubbles from the contrast media. The rate of refill of this space can be quantified. Increased rates of refill can be associated with active BAT depots. In another embodiment, a contrast media containing a fluorescent media can be used to locate BAT. The contrast media can be injected into a patient whose BAT has been activated. A needle based probe can be placed in the region of interest that is capable of counting the amount of fluorescent contrast that passes the probe. Increased counts per unit time correspond to increased blood flow and can be associated with activated BAT depots. Because humans can have a relatively small amount of BAT and because it can be difficult to predict where BAT is most prevalent even near a typical BAT depot such as the nape of the neck, imaging a patient to more accurately pinpoint BAT depots can allow more nerves innervating BAT to be stimulated and with greater precision. Any number of BAT depots identified through patient imaging can be marked for future reference using a permanent or temporary marker. As will be appreciated by a person skilled in the art, any type of marker can be used to mark a BAT depot, e.g., ink applied on and/or below the epidermis, a dye injection, etc. The marker can be configured to only be visible under special lighting conditions such as an ultraviolet light, e.g., a black light.

Whether BAT is activated directly and/or transcutaneously, target cellular areas for BAT nerve stimulation and/or direct stimulation of brown adipocytes can include cell surface receptors (e.g., TGR5, $\beta_1AR$, $\beta_2AR$, $\beta_3AR$, etc.), nuclear receptors (e.g., PPAR$\gamma$, FXR, RXR, etc.), transcription co-activators and co-repressors (e.g., PGC1$\alpha$, etc.), intracellular molecules (e.g., 2-deiodinase, MAP kinase, etc.), UCP1 activators, individual cells and related components (e.g., cell surface, mitochondria, and organelles), transport proteins, PKA activity, perilipin and HSL (phospho PKA substrate), CREBP (cAMP response element-binding protein), adenosine monophosphate-activated protein kinase (AMPK), bile acid receptors (e.g., TGR5, FGF15, FXR, RXR $\alpha$, etc.), muscarinic receptors, etc.

In the course of treating a patient, BAT nerves and/or brown adipocytes can be stimulated at any one or more BAT depots directly or indirectly and can be stimulated simultaneously, e.g., two or more BAT depots being concurrently stimulated, or stimulated sequentially, e.g., different BAT depots being stimulated at different times. Simultaneous stimulation of BAT can help encourage more and/or faster energy expenditure. Sequential stimulation of BAT can help prevent the "burning out" of target nerves and can help stimulate the creation of new BAT cells. Sequential nerve stimulation can include stimulating the same BAT depot more than once, with at least one other BAT depot being activated before activating a previously activated BAT depot. Simultaneous and/or sequential stimulation can help prevent tachypylaxis.

Figure 5:
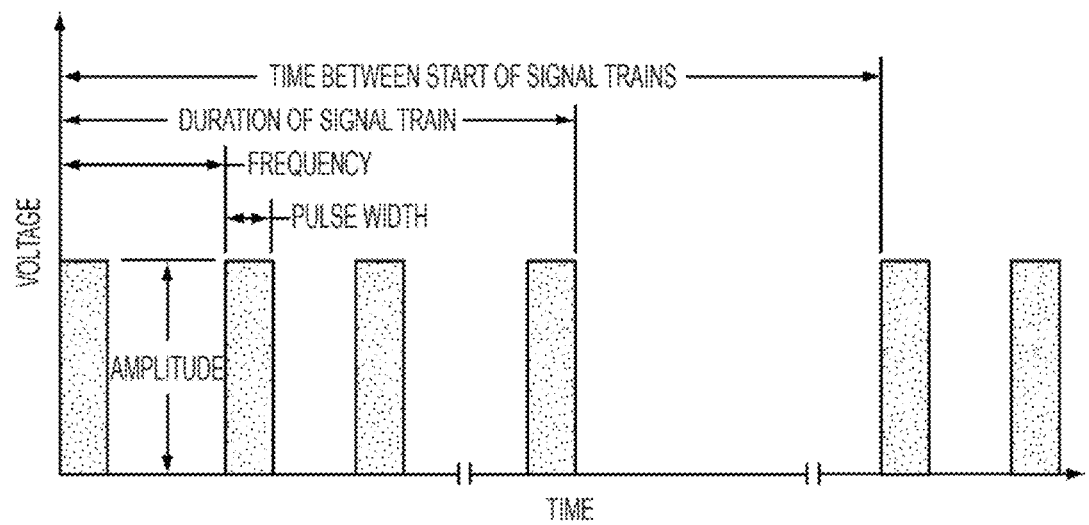
FIG. 5 is a graph showing voltage v. time for a generic electrical signal.

The electrical signal, whether transcutaneously or directly delivered, can be configured in a variety of ways. The stimulation "on" time amplitude can be higher for shorter periods and increased or decreased for longer periods of application. The electrical signal can have any "geometry" of the applied voltage, e.g., square waves, ramp waves, sine waves, triangular waves, and waveforms that contain multiple geometries. FIG. 5 illustrates amplitude, pulse width, activation signal pulse frequency, duration of signal train, and a time between start of signal trains for a generic (without any specified numerical parameters) electrical signal. In an exemplary embodiment, an electrical signal delivered to BAT can have a voltage having an amplitude in a range of about 1 to 20 V, e.g., about 10 V, e.g., about 4 V, about 7 V, etc.; a current having an amplitude in a range of about 2 to 6 mA, e.g., about 3 mA; a pulse width in a range about 10 $\mu$s to 40 ms, e.g., about 0.1 ms, about 2 ms, about 20 ms, etc.; an activation signal pulse frequency in a range of about 0.1 to 40 Hz, e.g., about 6 Hz or in a range of about 1 to 20 Hz; and a duration of signal train in a range of about 1 second to continuous, e.g., about 30 seconds, etc. A time between start of signal trains for a noncontinuous electrical signal delivered to BAT can be of any regular, predictable duration, e.g., hourly, daily, coordinated around circadian, ultradian, or other cycles of interest, etc., such as about ten minutes or about ninety minutes, or can be of any irregular, unpredictable duration, e.g., in response to one or more predetermined trigger events, as discussed further below.

Figure 6:
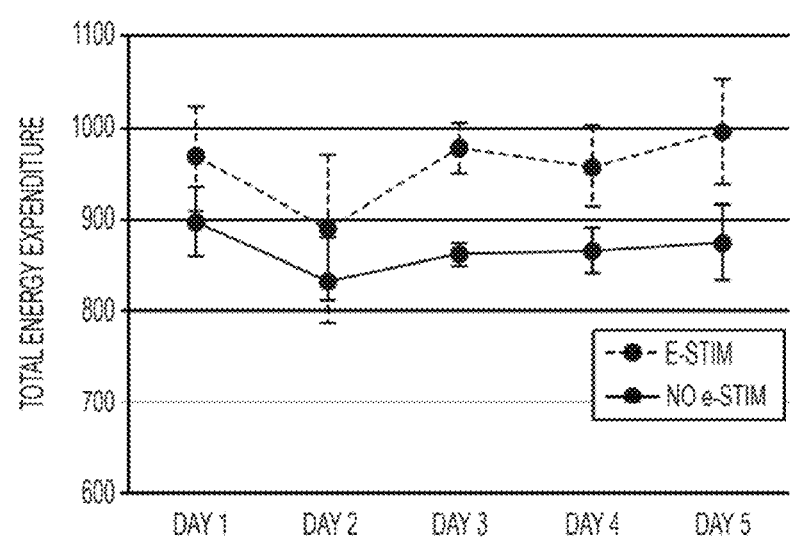
FIG. 6 is a graph showing total energy expenditure v. time for an experimental, continuous, direct electrical signal delivered to BAT depots in a group of subjects and showing total energy expenditure v. time for a group of non-stimulated control subjects.

In one non-limiting example, an electrical signal continuously delivered to BAT can be a pulse having an amplitude of about 7 V, a pulse width of about 0.1 ms, an activation signal pulse frequency of about 6 Hz. FIG. 6 shows one example of a graph of total energy expenditure v. time of continuous direct delivery of this electrical signal via implanted device to an interscapular BAT depot over a period of five days. Results of electrical stimulation using this electrical signal is shown by the graph line beginning at about 970 at Day 1, and a control of non-electrical stimulation is shown by the graph line beginning at about 900 at Day 1. As illustrated in the graph, the electrical signal delivery can lead to a sustained increase in oxygen consumption, which is correlated with increases in energy expenditure in the subjects, which are rats in the illustrated example. Over time, the increases in energy expenditure can lead to weight loss. Activity of the subjects receiving this electrical signal over the five day period was observed to be similar to activity of the subjects not receiving electrical stimulation over the five day period, thereby indicating that the illustrated increased energy expenditure of the stimulated subjects was due to the electrical stimulation and not due to increased physical activity and that the subjects were behaving normally during the stimulation treatment.

Figure 7:
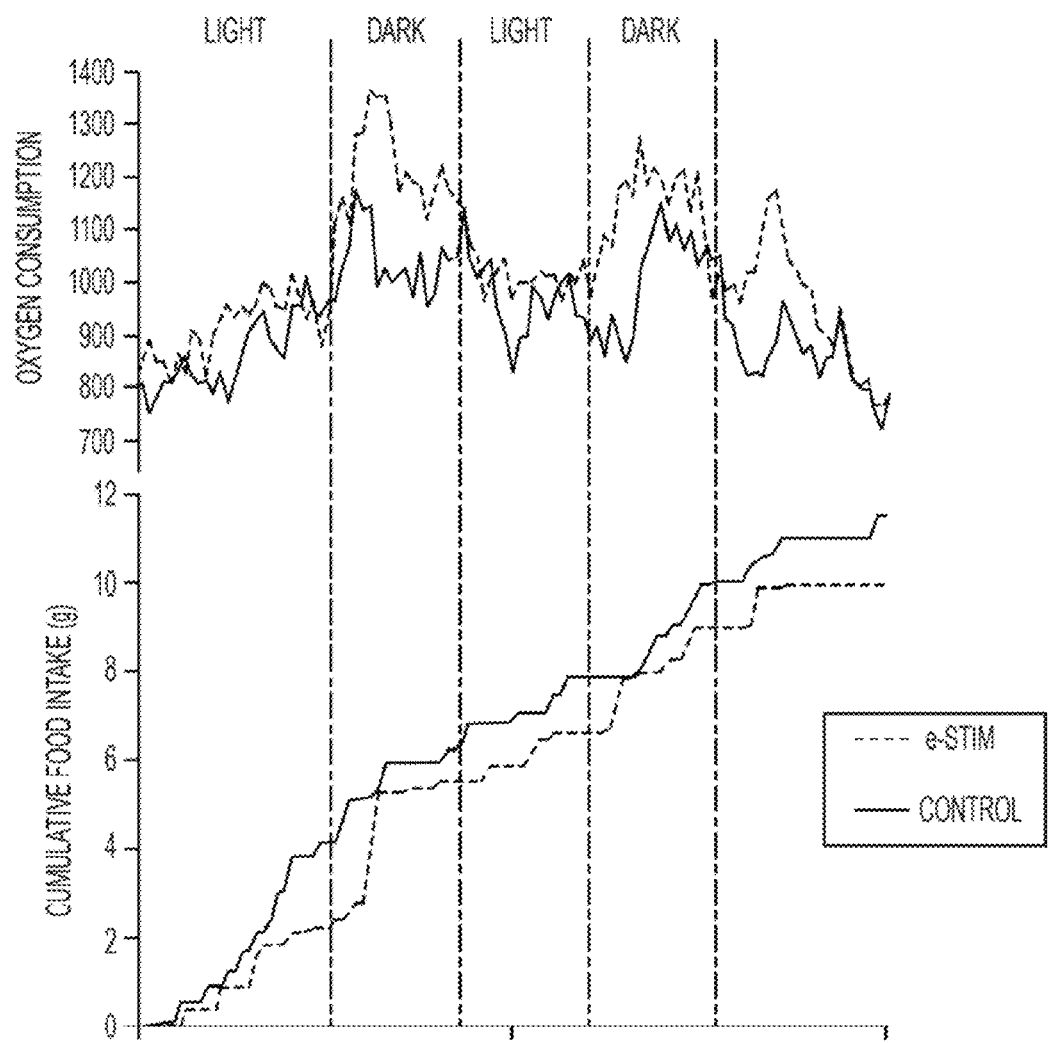
FIG. 7 is a graph showing a first plot of oxygen consumption v. time for the experimental, continuous, direct electrical signal delivered to BAT depots in the group of subjects of FIG. 6 and showing oxygen consumption v. time for the group of non-stimulated control subjects of FIG. 6, and showing a second plot of cumulative food intake v. time for the experimental, continuous, direct electrical signal delivered to BAT depots in the group of subjects of FIG. 6 and showing cumulative food intake v. time for the group of non-stimulated control subjects of FIG. 6.
Figure 8:
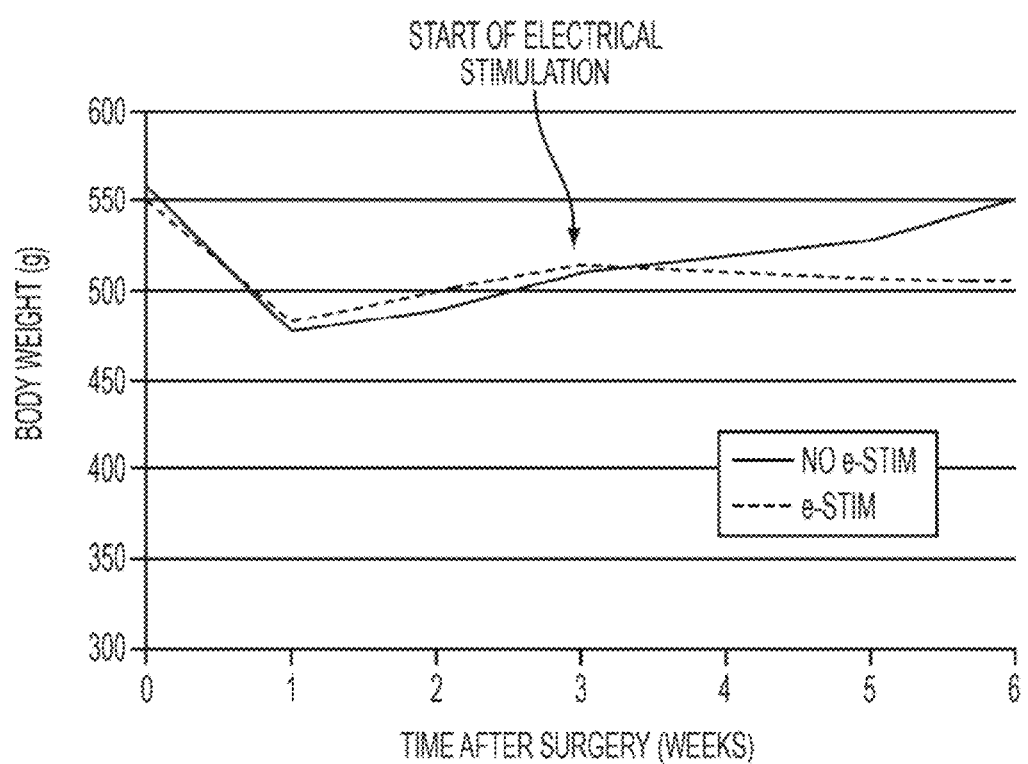
FIG. 8 is a graph showing body weight v. time for the experimental, continuous, direct electrical signal delivered to BAT depots in the group of subjects of FIG. 6 and showing body weight v. time for the group of non-stimulated control subjects of FIG. 6.

Oxygen consumption is plotted versus time for a 48 hour period in one example of a graph in FIG. 7 in which measurements were taken every 10 minutes. In the top plot in FIG. 7, results of electrical stimulation using this electrical signal are shown by the graph line beginning at about 825 at time zero, and a control of non-electrical stimulation is shown by the graph line beginning at about 800 at time zero. In the bottom plot of FIG. 7, results of electrical stimulation using this electrical signal are shown by the graph line which is at about 9 g at an end of the 48 time period, and a control of non electrical stimulation is shown by the graph line which is at about 11 g at the end of the 48 time period. Sustained moderate increases in energy expenditure were present for the electrically stimulated animals in the two light time periods, e.g., times when the animals were at rest, while more pronounced increases in energy expenditure were present for the electrically stimulated animals in the two dark time periods, e.g., when the animals were active and eating. Thus, when subjects stimulated with this electrical signal were active and eating, energy expenditure increased substantially, whereas moderate increases were observed at rest. Such an increase is consistent with diet-induced thermogenesis. The increase also demonstrates that continuous direct electrical stimulation can help ensure that at any time a subject eats, stimulated BAT can be ready to take the consumed calories and turn them into heat, thereby encouraging weight loss over time, as shown in one example of a graph in FIG. 8. Body weight is plotted versus time for a six week period in FIG. 8, with time zero representing a time of surgery to implant electrodes, which was performed on all subjects, and with week three marking a start time of electrical stimulation for the non-control group subjects. Results of electrical stimulation using this electrical signal are shown by the graph line beginning at about 550 g at time zero, and a control of non-electrical stimulation is shown by the graph line beginning at about 560 g at time zero. FIG. 8 illustrates that upon the start of electrical stimulation of BAT at week three, the electrically stimulated animals experienced continual weight loss until at least week six. In contrast, the control, non-electrically stimulated animals gained weight during the same period starting at week three, resulting in a difference in weight of about 15 percent between the stimulated group and the non-stimulated group.

Figure 9:
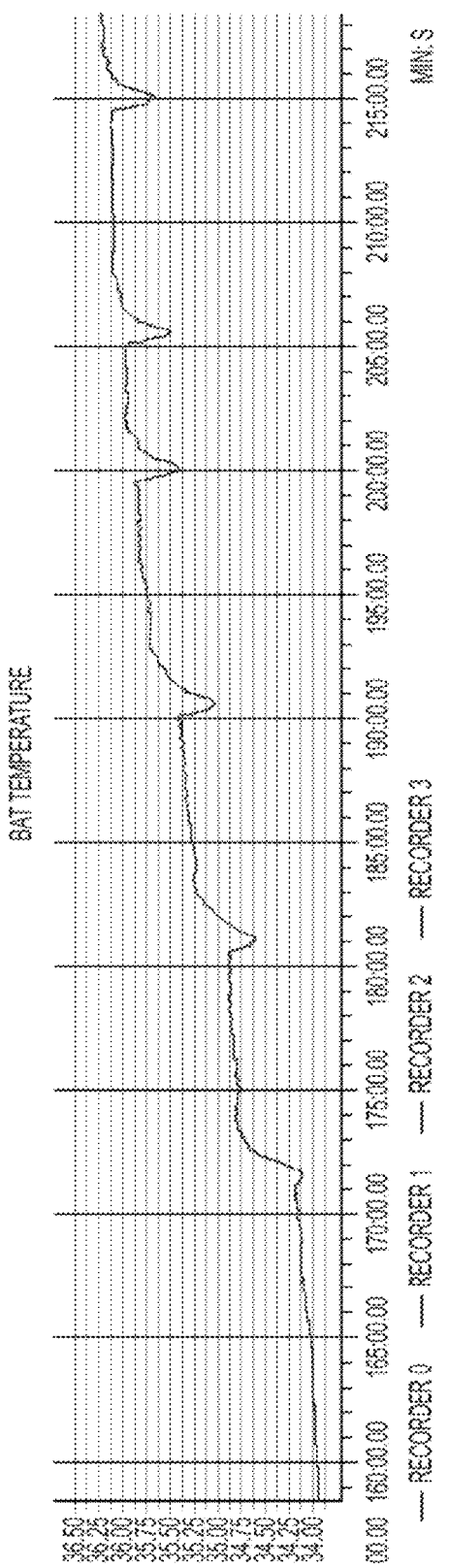
FIG. 9 is a graph showing BAT temperature v. time for an experimental, intermittent, direct electrical signal delivered to BAT depots in one subject.

In another non-limiting example, an electrical signal delivered to BAT can be a pulse having an amplitude of about 4 V, a pulse width of about 20 ms, an activation signal pulse frequency of about 6 Hz, a duration of signal train of about 30 seconds, and a time between start of signal trains of about 10 minutes. FIG. 9 shows one example of a graph of BAT temperature in degrees Celsius v. time of intermittent direct delivery of this electrical signal to a BAT depot of one patient. As illustrated in the graph, the electrical signal delivery can lead to a sustained increase in BAT temperature, which can be associated with a lagging increase in core temperature of the subjects, which are rats in the illustrated example. Over time, the sustained increase in BAT temperature can lead to weight loss.

Figure 10:
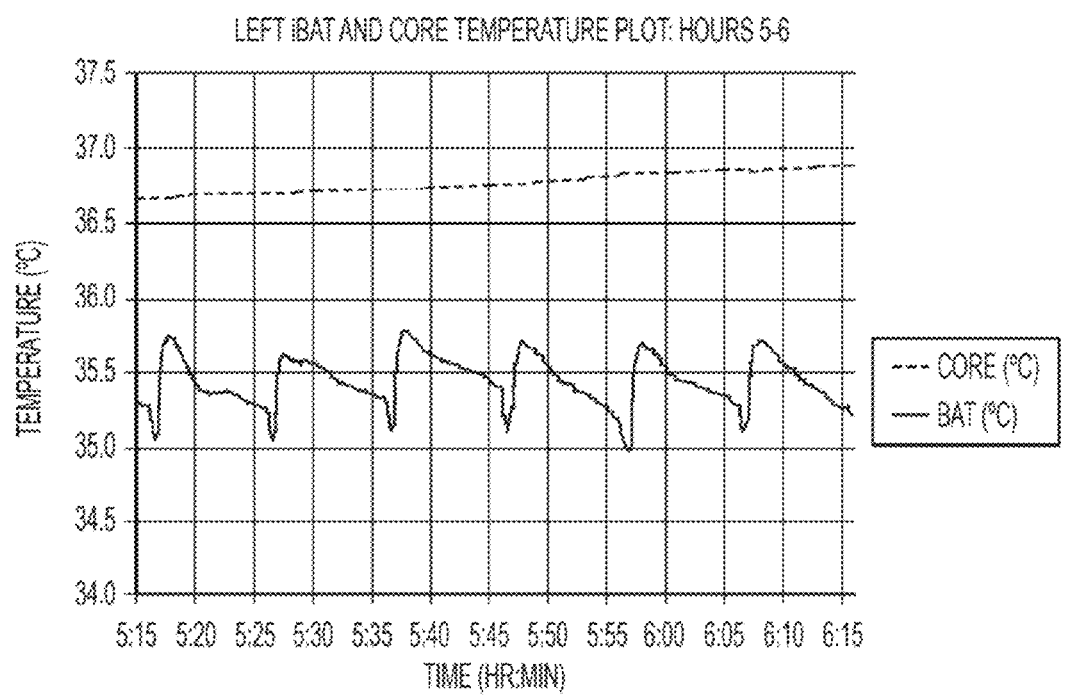
FIG. 10 is a graph showing BAT and core temperatures v. time for an experimental, intermittent, direct electrical signal delivered to BAT depots in one subject.

In another non-limiting example, an electrical signal delivered to BAT can be a pulse having an amplitude of about 10 V, a pulse width of about 2 ms, an activation signal pulse frequency of about 6 Hz, a duration of signal train of about 30 seconds, and a time between start of signal trains of about 10 minutes. FIG. 10 shows one example of a graph of BAT temperature v. time of intermittent direct delivery of this electrical signal to a BAT depot of one patient during hours 5 and 6 of continuous electrical signal delivery to subjects (rats in this illustrated example). Core temperature is shown by the graph line beginning at about 36.7° C. at time 5:15, and BAT temperature is shown by the graph line beginning at about 35.3° C. at time 5:15. As illustrated in the graph, the electrical signal delivery can lead to a sustained activation of BAT. Over time, the sustained activation of BAT can lead to weight loss.

In another non-limiting example, an electrical signal delivered to BAT can be configured as a monophasic square pulse having a square wave shape, a voltage alternating in amplitude from about 0 to 20 V, an activation signal pulse frequency in a range of about 5 to 10 Hz, a pulse width (duration) of about 2 ms, a pulse train on/off time of about 20 seconds "on" and about 40 seconds "off," and a treatment time of about 11 minutes, as described in more detail in Shimizu et al., "Sympathetic Activation of Glucose Utilization in Brown Adipose Tissue in Rats," Journal of Biochemistry, Vol. 110, No. 5, 1991, pgs 688-692. Further non-limiting examples of electrical signals that can be delivered to BAT are described in more detail in Flaim et al., "Functional and Anatomical Characteristics of the Nerve-Brown Adipose Interation in the Rat," Pflügers Arch., 365, 9-14 (1976); Minokoshi et al., "Sympathetic Activation of Lipid Synthesis in Brown Adipose Tissue in the Rat," J. Psysio. (1988) 398, 361-70; Horwitz et al., "Norepinephrine-Induced Depolarization of Brown Fat Cells." Physiology (1969) 64, 113-20; and U.S. Pat. Pub. No. 2010/0312295 filed May 5, 2010 entitled "Brown Adipose Tissue Utilization Through Neuromodulation."

In one embodiment, the same electrical signal can be delivered to a particular BAT depot, either continuously or sequentially. In another embodiment, a first electrical signal can be transcutaneously or directly delivered to a particular BAT depot, and then subsequently, either immediately thereafter or after a passage of a period of time, a second, different electrical signal can be delivered to the same particular BAT depot. In this way, chances of a BAT depot adapting to a particular electrical signal can be reduced, thereby helping to prevent the BAT depot from becoming less receptive to electrical stimulation.

Whether a continuous electrical signal or an intermittent electrical signal is transcutaneously delivered, e.g., with a transdermal patch as discussed further below, or subcutaneously delivered via an at least partially implanted device, the electrical signal can include a low frequency modulating signal and a high frequency carrier signal. Generally, the high frequency carrier signal can be used to pass through high impedance tissue (subcutaneous or transcutaneous) while the modulating signal can be used to activate nervous tissue and/or electrically responsive brown adipocytes. The waveform can be generated by modulating a carrier waveform with a pulse envelope. Properties of the carrier waveform such as amplitude, frequency, and the like, can be chosen so as to overcome the tissue impedance and the stimulation threshold of the target nerve. The pulse envelope can be a waveform having a specific pulse width, amplitude and shape designed to selectively stimulate the target nerve. This waveform can be able to penetrate efficiently through tissue, such as skin, to reach the target nerve with minimal loss in the strength of the electrical signal, thereby saving battery power that would otherwise have been used in several attempts to stimulate the target nerve with low frequency signals. Moreover, only the target nerve is stimulated, and non-target nerves, e.g., nerves associated with pain, are not stimulated. Exemplary embodiments of methods and devices for applying a signal including a high frequency carrier signal are described in more detail in U.S. Pat. Pub. No. 2009/0093858 filed Oct. 3, 2007 and entitled "Implantable Pulse Generators And Methods For Selective Nerve Stimulation," U.S. Pat. Pub. No. 2005/0277998 filed Jun. 7, 2005 and entitled "System And Method For Nerve Stimulation," and U.S. Pat. Pub. No. 2006/0195153 filed Jan. 31, 2006 and entitled "System And Method For Selectively Stimulating Different Body Parts."

Figure 11:
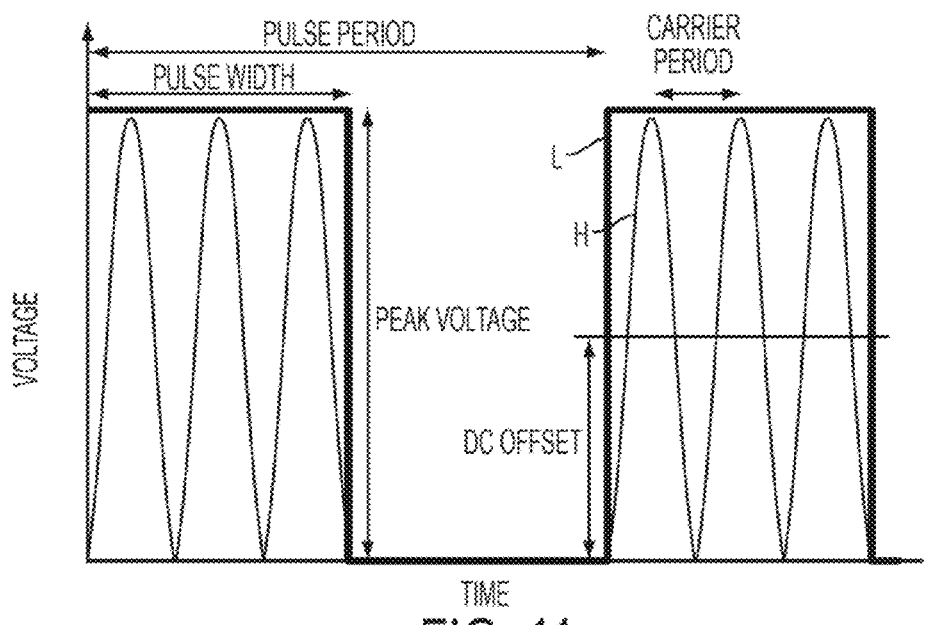
FIG. 11 is a graph showing voltage v. time for a generic electrical signal including a low frequency modulating signal and a high frequency carrier signal.

The low frequency modulating signal and a high frequency carrier signal can each have a variety of values and configurations. The low frequency modulating signal can be, e.g., a signal having an activation signal pulse frequency in a range of about 0.1 to 100 Hz, e.g., in a range of about 0.1 to 40 Hz, e.g., less than about 10 Hz. The high frequency carrier signal can be, e.g., in a range of about 10 to 400 kHz, e.g., in a range of about 200 to 250 kHz. Pulse widths can also vary, e.g., be in a range of about 10 µs to 10 ms, e.g., less than about 2 ms. In one exemplary embodiment, the electrical signal can have a modulating signal in a range of about 2 to 15 Hz, e.g., about 6 Hz, a carrier frequency of about 210 kHz, and a pulse width in a range of about 0.1 to 2 ms. FIG. 11 illustrates a generic (without any specified numerical parameters) electrical signal including a low frequency modulating signal L and a high frequency carrier signal H.

Generally, low frequency signals can cause activation of Types A and B fibers, e.g., myelinated neurons, and Type C fibers, e.g., unmyelinated neurons. The signal to activate Type C fibers can be greater than, e.g., a longer pulse width and a higher current amplitude, than a signal to activate Type A and B fibers. Postganglionic fibers innervating BAT depots likely include Type C fibers, thereby allowing a BAT depot to be activated by a low frequency signal, e.g., a signal less than about 10 Hz and having a pulse width greater than about 300 µs. Preganglionic nerves such as small diameter, unmyelinated Type C fibers and small diameter, myelinated Type B fibers may also innervate BAT, thereby also allowing a BAT depot to be activated by a low frequency signal, e.g., a signal in a range of about 10 to 40 Hz and having a pulse width less than about 200 µs.

An electrical signal delivered to a BAT depot can be applied continuously, in predetermined intervals, in sporadic or random intervals, in response to one or more predetermined trigger events, or in any combination thereof. If the signal is continuously delivered to the patient, particular care should be taken to ensure that the signal delivered to the patient will not damage the target nerves or tissues. For one non-limiting example, nerve or tissue damage can be reduced, if not entirely prevented, by continuously delivering an electrical signal via en electrode having a relatively large surface area to help distribute an electrical signal's energy between multiple nerves. For electrical signals delivered intermittently, nerve damage can be reduced, if not entirely prevented, by selecting an on/off ratio in which the signal is "off" for more time than it is "on." For non-limiting example, delivering an electrical signal to BAT intermittently with an on/off ratio of about 1:19, e.g., electrical signals delivered for 30 seconds every ten minutes (30 seconds on/9.5 minutes off), can help reduce or entirely prevent nerve damage. The device delivering the electrical signal can be configured to respond to one or more predetermined trigger events, e.g., events that are sensed by or otherwise signaled to the device. Non-limiting examples of trigger events include the patient eating, the patient resting (e.g., sleeping), a threshold temperature of the patient (e.g., a temperature in the stimulated BAT depot or a core temperature), a directional orientation of the patient (e.g., recumbent as common when sleeping), a change in the patient's weight, a change in the patient's tissue impedance, manual activation by the patient or other human (e.g., via an onboard controller, via a wired or wirelessly connected controller, or upon skin contact), a blood chemistry change in the patient (e.g., a hormonal change), low energy expenditure, menstrual cycles in women, medication intake (e.g., an appetite suppressant such as topiramate, fenfluramine, etc.), an ultradian or other circadian rhythm of the patient, and a manually-generated or automatically-generated signal from a controller in electronic communication, wired and/or wireless, with the device. In one embodiment, the patient eating can be determined through a detection of heart rate variability, as discussed in more detail in U.S. patent application Ser. No. 12/980,965 filed on Dec. 29, 2010 and entitled "Obesity Therapy And Heart Rate Variability" and U.S. patent application Ser. No. 12/980,710 filed on Dec. 29, 2010 and entitled "Obesity Therapy And Heart Rate Variability". The controller can be internal to the device, be located external from but locally to device, or be located external and remotely from device. As will be appreciated by a person skilled in the art, the controller can be coupled to the device in any way, e.g., hard-wired thereto, in wireless electronic communication therewith, etc. In some embodiments, multiple devices can be applied a patient, and at least two of those devices can be configured to deliver an electrical signal based on different individual trigger events or combinations of trigger events.

Figure 12:
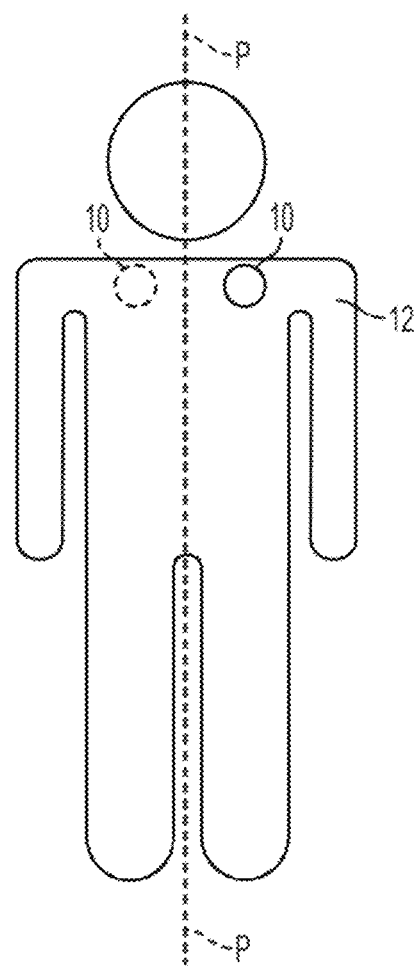
FIG. 12 is a front view of a body showing one embodiment of an electrical stimulation device positioned on opposite sides of the body's sagittal plane.

Generally, transcutaneous stimulation of BAT can include applying a device to an exterior skin surface of a patient proximate to a BAT depot and activating the device to deliver an electrical signal to the BAT depot. In this way, the electrical signal can activate the BAT proximate to the device by stimulating the nerves innervating the BAT and/or by stimulating brown adipocytes directly. As mentioned above, two or more transcutaneous devices, same or different from one another, can be simultaneously applied to a patient, proximate to the same BAT depot or to different BAT depots. Although a patient can have two or more transcutaneously applied devices and although the devices can be configured to simultaneously deliver electrical signals to BAT, the devices can be configured such that only one delivers an electrical signal at a time. As also mentioned above, a transcutaneous device can be rotated to different BAT depots of a patient and deliver an electrical signal to each of the BAT depots. Rotating a device between two or more different locations on a patient's body and/or removing a device from a patient when not in use can help prevent nerve or tissue desensitization and/or dysfunction, can help reduce any adverse effects of a device's attachment to the body, e.g., irritation from an adhesive applying a device to skin, and/or can help stimulate creation or replication of new BAT in multiple locations on a patient's body. For non-limiting example, the device can be placed in varying positions on the body to modulate the activity of different regions of BAT. In one embodiment, the device can be worn on one side of the neck, e.g., the left side, for a period of time and then on an opposite side of the neck, e.g., the right side, for the next time period, etc. In another embodiment, the device can be worn on an anterior side of a BAT depot, e.g., front of a left shoulder on one side of the patient's coronal plane, for a period of time and then on an opposite, posterior side of the BAT depot, e.g., back of the left shoulder on the opposite side of the patient's coronal plane, for the next period of time. In yet another embodiment, illustrated in FIG. 12, a device 10 can be worn proximate a BAT depot on one of a left and right side of a sagittal plane P in a supraclavicular region of a body 12 for a period of time and then the device 10 can be worn on the other of the left and right sides of the sagittal plane P in the supraclavicular region proximate to another BAT depot for the next period of time. Although the same device 10 is shown in FIG. 12 as being sequentially relocated to different tissue surface or skin positions on the body 12, as discussed herein, one or both of the devices can be implanted and/or two separate devices can be used with a patient such that a first device is positioned at one location and a second device is positioned at a second, different location.

In one embodiment, a transcutaneous device can be positioned in a first location on a patient, e.g., a left supraclavicular region, for a first predetermined period of time, e.g., one week, and then relocated to a second location on the patient, e.g., a right supraclavicular region, for a second predetermined period of time, e.g., one week. The first and second predetermined periods of time can be the same as or different from one another. The first and second locations can mirror each other, e.g., on left and rights of a sagittal plane of the patient, or they can non-mirror images of one another. During the first predetermined period of time, the device can be configured to cycle in a diurnal pattern during waking hours between being "on" to electrically stimulate the patient, e.g., a 30 minute dose of electrical stimulation having any of the parameters discussed herein, and being "off" without delivering electrical stimulation to the patient, e.g., a one hour period of no stimulation. The electrical signal, e.g., an electrical signal including modulating and carrier signals, delivered when the device is "on" can be continuous, can ramp up at a start of the "on" time to a predetermined maximum level, such as a level set by a physician during an initial patient visit, can ramp down at an end of the "on" time, and can be substantially constant between the ramp up and ramp down times. The signal can ramp up and down in any amount of time, e.g., in less than about five minutes. Such a cycle can be repeated about twelve time per day during each of the first and second predetermined periods of time, and during any subsequent periods of time, e.g., repeatedly switching the device every other week between the first and second locations.

In another embodiment, a transcutaneous device can be positioned on an exterior skin surface of a patient and be configured to electrically stimulate the patient in a natural mimicking pattern for a time period of at least one week. The device can be relocated to a different location on the patient's skin and stimulate the patient at the different location in the natural mimicking pattern for another time period of at least one week. The device can continue being located and relocated for any number of weeks. The electrical stimulation can include a fixed carrier frequency and a variable modulating frequency configured to vary based on nutrient and mechanoreceptors that indicate the patient eating. In other words, the modulating frequency can mimic stomach distension of the patient.

In still another embodiment, a transcutaneous device can be positioned on an exterior skin surface of a patient and be configured to intermittently electrically stimulate the patient at a constant intensity, e.g., cycle between an "on" configuration delivering an electrical signal at the constant intensity to the patient and an "off" configuration without delivering any electrical signal to the patient. The delivered electrical signal can ramp up at a start of an "on" time period to the constant intensity, and can ramp down at an end of the "on" time period from the constant intensity. The signal can ramp up and down in any amount of time, such as ramp up for about ¼ of a total "on" time, deliver the signal at the constant intensity for about ½ of the total "on" time, and ramp down for about ¼ of the total "on" time. In one embodiment, the device can ramp up from about 0 Hz to about 20 Hz in about 15 minutes, stimulate at about 20 Hz for about 35 minutes, and ramp down from about 20 Hz to about 0 Hz in about 10 minutes for a total "on" time of about 50 minutes.

The transcutaneous device used to transcutaneously activate BAT can have a variety of sizes, shapes, and configurations. Generally, the device can be configured to generate and/or deliver an electrical signal to tissue at predetermined intervals, in response to a manual trigger by the patient or other human, in response to a predetermined trigger event, or any combination thereof. As will be appreciated by a person skilled in the art, and as discussed in more detail above and in U.S. Pat. Pub. No. 2009/0093858 filed Oct. 3, 2007 and entitled "Implantable Pulse Generators And Methods For Selective Nerve Stimulation," the body attenuates low frequency signals requiring a high frequency signal for transdermal passage. This high-frequency or carrier signal, in conjunction with a modulating low frequency wave can be applied by the transcutaneous device to stimulate the nerves innervating BAT for FFA or other lipid consumption leading to loss of body fat and body weight.

Figure 13:
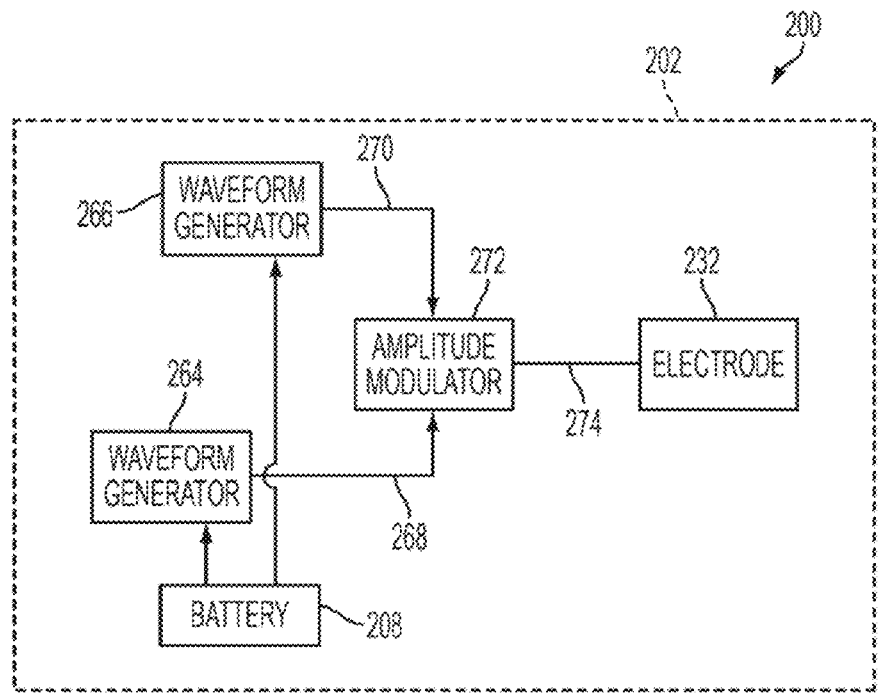
FIG. 13 is a schematic view of one embodiment of a transcutaneous device for stimulating BAT.

FIG. 13 illustrates one exemplary embodiment of a transcutaneous device 200 in the form of a selective nerve stimulation patch housing configured to generate and deliver an electrical signal to tissue such as BAT. The device 200 includes a circuitized substrate 202 configured to generate electrical signals for stimulating tissue such as BAT. The device 200 can include a suitable power source or battery 208, e.g., a lithium battery, a first waveform generator 264, and a second waveform generator 266. The first and second waveform generators 264, 266 can be electrically coupled to and powered by the battery 208. The waveform generators 264, 266 can be of any suitable type, such as those sold by Texas Instruments of Dallas, Tex. under model number NE555. The first waveform generator 264 can be configured to generate a first waveform or low frequency modulating signal 268, and the second waveform generator 266 can be configured to generate a second waveform or carrier signal 270 having a higher frequency than the first waveform 268. As discussed herein, such low frequency modulating signals cannot, in and of themselves, pass through body tissue to effectively stimulate target nerves. The second waveform 270 can, however, to overcome this problem and penetrate through body tissue. The second waveform 270 can be applied along with the first waveform 268 to an amplitude modulator 272, such as the modulator having the designation On-Semi MC1496, which is sold by Texas Instruments.

Figure 14:
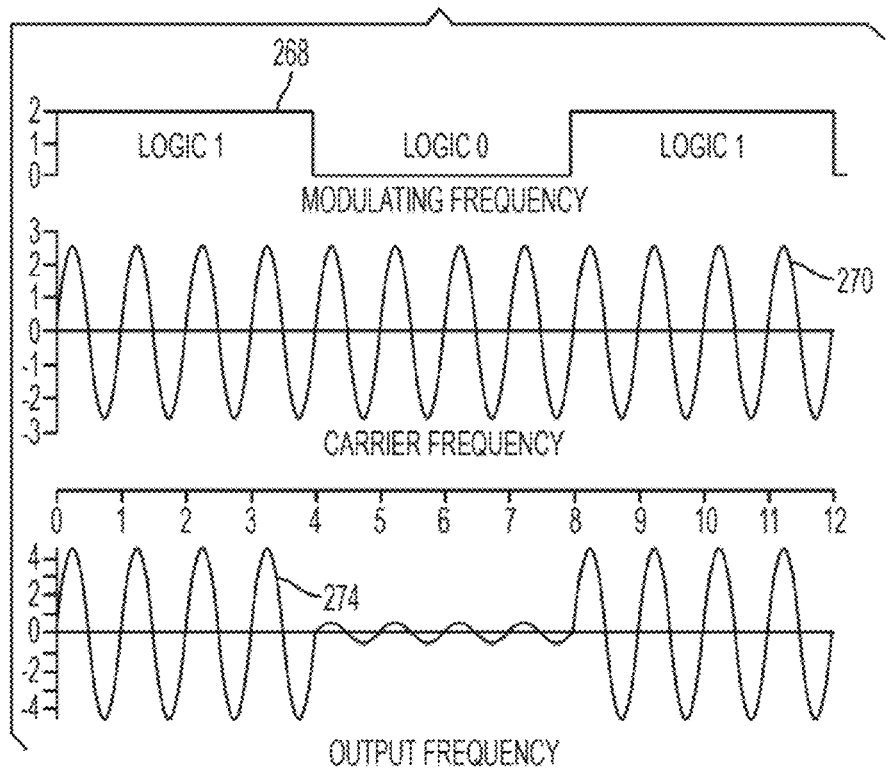
FIG. 14 is a plurality of graphs showing exemplary waveforms generated by the transcutaneous device of FIG. 13.

The modulator 272 can be configured to generate a modulated waveform 274 that is transmitted to one or more electrodes 232 accessible at a bottom surface of the circuitized substrate 202. Although FIG. 13 shows only one electrode 232, the device 200 can include two or more electrodes. The electrodes 232 can be configured to, in turn, apply the modulated waveform 274 to a target nerve to stimulate the target nerve. As illustrated in FIGS. 13 and 14, the first waveform 268 can be a square wave, and the second waveform 270 can be a sinusoidal signal. As will be appreciated by a person skilled in the art, modulation of the first waveform 268 with the second waveform 270 can results in a modulated waveform or signal 274 having the configuration shown in FIG. 14. Although the signals in FIG. 14 are illustrated as being biphasic, the signals can be monophasic.

Various exemplary embodiments of transcutaneous devices configured to apply an electrical signal or other stimulation means to stimulate nerves are described in more detail in U.S. Pat. Pub. No. 2009/0132018 filed Nov. 16, 2007 and entitled "Nerve Stimulation Patches And Methods For Stimulating Selected Nerves," U.S. Pat. Pub. No. 2008/0147146 filed Dec. 19, 2006 and entitled "Electrode Patch And Method For Neurostimulation," U.S. Pat. Pub. No. 2005/0277998 filed Jun. 7, 2005 and entitled "System And Method For Nerve Stimulation," U.S. Pat. Pub. No. 2006/0195153 filed Jan. 31, 2006 and entitled "System And Method For Selectively Stimulating Different Body Parts," U.S. Pat. Pub. No. 2007/0185541 filed Aug. 2, 2006 and entitled "Conductive Mesh For Neurostimulation," U.S. Pat. Pub. No. 2006/0195146 filed Jan. 31, 2006 and entitled "System And Method For Selectively Stimulating Different Body Parts," U.S. Pat. Pub. No. 2008/0132962 filed Dec. 1, 2006 and entitled "System And Method For Affecting Gastric Functions," U.S. Pat. Pub. No. 2008/0147146 filed Dec. 19, 2006 and entitled "Electrode Patch And Method For Neurostimulation," U.S. Pat. Pub. No. 2009/0157149 filed Dec. 14, 2007 and entitled "Dermatome Stimulation Devices And Methods," U.S. Pat. Pub. No. 2009/0149918 filed Dec. 6, 2007 and entitled "Implantable Antenna," U.S. Pat. Pub. No. 2009/0132018 filed Nov. 16, 2007 and entitled "Nerve Stimulation Patches And Methods For Stimulating Selected Nerves," U.S. patent application Ser. No. 12/317,193 filed Dec. 19, 2008 and entitled "Optimizing The Stimulus Current In A Surface Based Stimulation Device," U.S. patent application Ser. No. 12/317,194 filed Dec. 19, 2008 and entitled "Optimizing Stimulation Therapy Of An External Stimulating Device Based On Firing Of Action Potential In Target Nerve," U.S. patent application Ser. No. 12/407,840 filed Mar. 20, 2009 and entitled "Self-Locating, Multiple Application, And Multiple Location Medical Patch Systems And Methods Therefor," U.S. patent application Ser. No. 12/605,409 filed Oct. 26, 2009 and entitled "Offset Electrodes."

In an exemplary embodiment, the transcutaneous device can include an electrical stimulation patch configured to be applied to an external skin surface and to deliver an electrical signal to tissue below the skin surface, e.g., to underlying BAT. The patch can be configured to generate its own electrical signal with a signal generator and/or to deliver an electrical signal received by the patch from a source in electronic communication with the patch. The device can be wireless and be powered by an on-board and/or external source, e.g., inductive power transmission. The patch can be attached to the skin in any way, as will be appreciated by a person skilled in the art. Non-limiting examples of patch application include using a skin adhesive locally (e.g., on patch rim), using a skin adhesive globally (e.g., on skin-contacting surfaces of the patch), using an overlying support (e.g., gauze with taped edges), using an adherent frame allowing interchangeability (e.g., a brace or an article of clothing), being subdermally placed with wireless connectivity (e.g., Bluetooth) or transdermal electrodes, and using any combination thereof. Electrodes can include receiver circuitry configured to interact with a controller in electronic communication with the electrodes such that the controller can control at least some functions of the electrodes, e.g., on/off status of the electrodes and adjustment of parameters such as amplitude, frequency, length of train, etc.

In use, and as mentioned above, an electrical stimulation patch can be worn continuously or intermittently as needed. In a transcutaneous application, a patch such as one described in previously mentioned U.S. Pat. Pub. No. 2009/0132018, can be designed to transmit through the skin using a dual waveform approach employing a first waveform designed to stimulated a nerve coupled with a high frequency carrier waveform. The patch can be placed proximate to a BAT depot, such as over the left supraclavicular region of the patient's back, for a predetermined amount of time, e.g., twelve hours, one day, less than one week, seven days (one week), one month (four weeks), etc., and can continuously deliver an electrical signal to the BAT. As mentioned above, the BAT depot can be identified by imaging the patient prior to application of the patch proximate to the BAT depot. Seven days is likely the longest period an adhesive can be made to stick to the skin of a patient without modification and can thus be a preferable predetermined amount of time for patches applied to skin with an adhesive. After the predetermined amount of time, the patch can be removed by a medical professional or the patient, and the same patch, or more preferably a new patch, can be placed, e.g., on the right supraclavicular region of the patient's back for another predetermined amount of time, which can be the same as or different from the predetermined amount of time as the first patch applied to the patient. This process can be repeated for the duration of the treatment, which can be days, weeks, months, or years. In some embodiments, the process can be repeated until occurrence of at least one threshold event, e.g., a predetermined amount of time, a predetermined physiological effect such as a predetermined amount of weight lost by the patient, etc. If the same patch is relocated from a first region, e.g., the left supraclavicular region, to a second region, right supraclavicular region, the patch can be reconditioned after removal from the first region and prior to placement at the second region. Reconditioning can include any one or more actions, as will be appreciated by a person skilled in the art, such as replacing one or more patch components, e.g., a battery, an adhesive, etc.; cleaning the patch; etc.

To more accurately simulate a weight loss surgery that has a continuous or chronic effect on a patient for an extended period of time, the patch can be placed on a patient and continuously or chronically deliver an electrical signal thereto for an extended, and preferably predetermined, amount of time. In an exemplary embodiment, the predetermined amount of time can be at least four weeks. The electrical signal can be delivered to same BAT depot for the predetermined amount of time, or two or more different BAT depots can be stimulated throughout the predetermined amount of time, e.g., left and right supraclavicular regions being stimulated for alternate periods of seven days to total one month of predetermined time. Continued or chronic nerve stimulation to activate BAT can increase BAT energy expenditure over time and potentially induce more or faster weight loss than periodic or intermittent nerve stimulation. The electrical signal can be the same or can vary during the amount of time such that the electrical signal is continuously and chronically applied to the patient to provide 24/7 treatment mimicking the 24/7 consequences of surgery. The continuous amount of time the patient is electrically stimulated can be a total amount of continuous activation of any one BAT depot (e.g., activation of a single BAT depot), sequential activation of two or more BAT depots, simultaneous activation of two or more BAT depots, or any combination thereof. A total amount of time of sequential activation of different BAT depots can be considered as one extended amount of time despite different areas of BAT activation because activation of one BAT depot may cause the brain to signal for BAT activation in other BAT depots.

Generally, direct activation of BAT can include implanting a device below the skin surface proximate to a BAT depot, e.g., within a BAT depot, and activating the device to deliver an electrical signal to the nerves innervating the BAT depot and/or to brown adipocytes directly. BAT itself is densely innervated, with each brown adipocyte being associated with its own nerve ending, which suggests that stimulating the BAT directly can target many if not all brown adipocytes and depolarize the nerves, leading to activation of BAT. The sympathetic nerves that innervate BAT can be accessed directly through standard surgical techniques, as will be appreciated by a person skilled in the art. The device can be implanted on a nerve or placed at or near a nerve cell's body or perikaryon, dendrites, telodendria, synapse, on myelin shelth, node of Ranvier, nucleus of Schwann, or other glial cell to stimulate the nerve. While implanting such a device can require a surgical procedure, such implantation is typically relatively short, outpatient, and with greatly reduced risks from longer and more complicated surgical procedures such as gastric bypass. In an exemplary embodiment, a stimulation device with at least two electrodes can be at least partially implanted in the patient, and more preferably entirely within the patient. A person skilled in the art will appreciate that any number of electrodes, e.g., one or more, can be at least partially implanted in the patient. The leads of the at least one electrode can be implanted in a location sufficiently close to the nerves innervating the BAT so that when activated, the signal sent through the at least one electrode is sufficiently transferred to adjacent nerves, causing these nerves to depolarize. As mentioned above, electrodes can include receiver circuitry configured to interact with a controller in electronic communication with the electrodes such that the controller can control at least some functions of the electrodes, e.g., on/off status of the electrodes and adjustment of parameters such as amplitude, frequency, length of train, etc.

Figure 15:
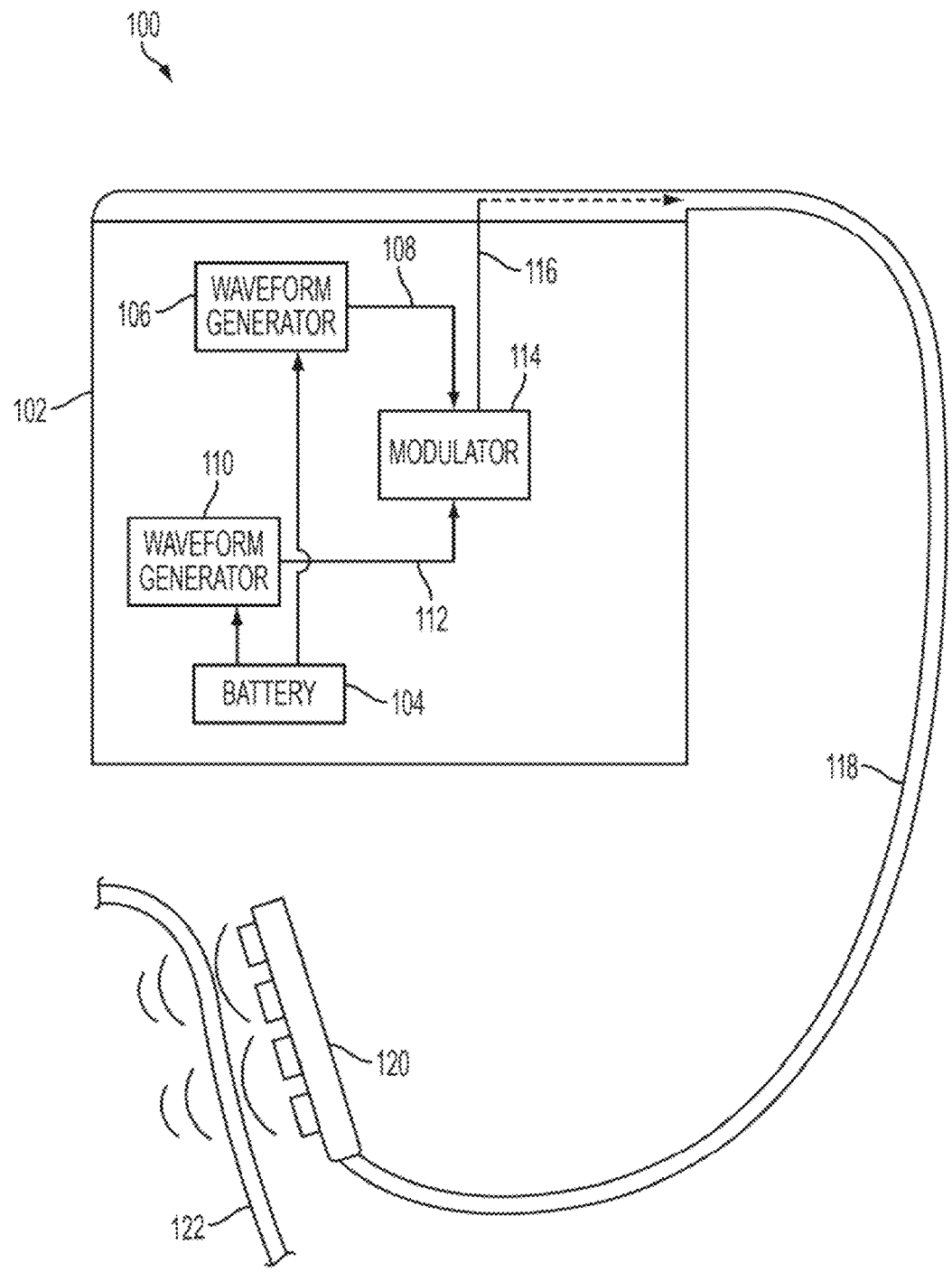
FIG. 15 is a schematic view of one embodiment of an implantable device for stimulating BAT.

FIG. 15 illustrates one exemplary embodiment of an implantable device 100 configured to generate and deliver an electrical signal to tissue such as BAT. The implantable device 100 can include a housing 102 coupled to a suitable power source or battery 104, such as a lithium battery, a first waveform generator 106, and a second waveform generator 108. As in the illustrated embodiment, the battery 104 and first and second waveform generators can be located within the housing 102. In another embodiment, a battery can be external to a housing and be wired or wirelessly coupled thereto. The housing 102 is preferably made of a biocompatible material. The first and second waveform generators 106, 108 can be electrically coupled to and powered by the battery 104. The waveform generators 106, 108 can be of any suitable type, such as those sold by Texas Instruments of Dallas, Tex. under model number NE555. The first waveform generator 106 can be configured to generate a first waveform or low frequency modulating signal 108, and the second waveform generator 110 can be configured to generate a second waveform or carrier signal 112 having a higher frequency than the first waveform 108. As discussed herein, such low frequency modulating signals cannot, in and of themselves, pass through body tissue to effectively stimulate target nerves. The second waveform 108 can, however, to overcome this problem and penetrate through body tissue. The second waveform 112 can be applied along with the first waveform 108 to an amplitude modulator 114, such as the modulator having the designation On-Semi MC1496, which is sold by Texas Instruments.

Figure 16:
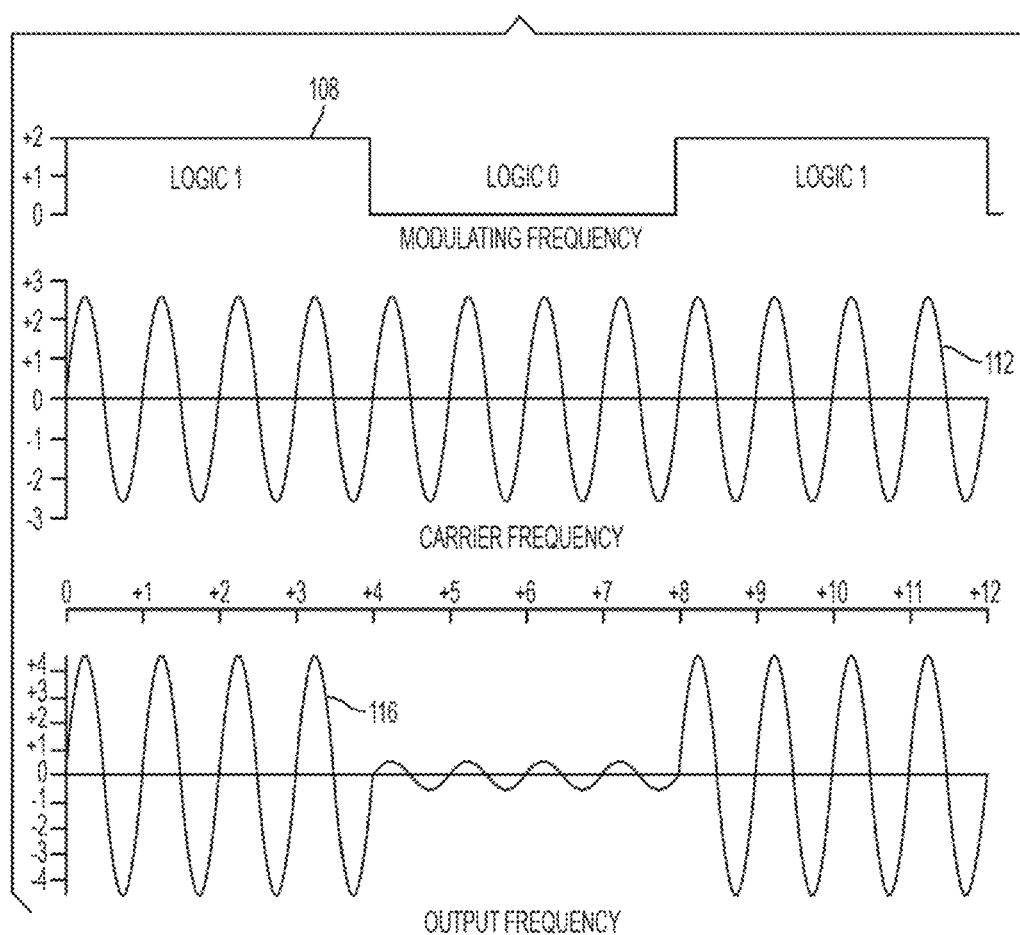
FIG. 16 is a plurality of graphs showing exemplary waveforms generated by the implantable device of FIG. 15.

The modulator 114 can be configured to generate a modulated waveform 116 that is transmitted through a lead 118 to one or more electrodes 120. Four electrodes are illustrated, but the device 100 can include any number of electrodes having any size and shape. The lead 118 can be flexible, as in the illustrated embodiment. The electrodes 120 can be configured to, in turn, apply the modulated waveform 116 to a target nerve 122 to stimulate the target nerve 122. As illustrated in FIGS. 15 and 16, the first waveform 108 can be a square wave, and the second waveform 112 can be a sinusoidal signal. As will be appreciated by a person skilled in the art, modulation of the first waveform 108 with the second waveform 112 can result in a modulated waveform or signal 116 having the configuration shown in FIG. 11.

If an electrode is implanted under a patient's skin, a waveform transmitted to the implanted electrode can include a modulating signal but not include a carrier signal because, if the implanted electrode is sufficiently near a BAT depot, the modulating signal alone can be sufficient to stimulate the target. The waveform transmitted to an implanted electrode can, however, include both a modulating signal and a carrier signal.

Various exemplary embodiments of devices configured to directly apply an electrical signal to stimulate nerves are described in more detail in U.S. Pat. Pub. No. 2005/0177067 filed Jan. 26, 2005 and entitled "System And Method For Urodynamic Evaluation Utilizing Micro-Electronic Mechanical System," U.S. Pat. Pub. No. 2008/0139875 filed Dec. 7, 2006 and entitled "System And Method For Urodynamic Evaluation Utilizing Micro Electro-Mechanical System Technology," U.S. Pat. Pub. No. 2009/0093858 filed Oct. 3, 2007 and entitled "Implantable Pulse Generators And Methods For Selective Nerve Stimulation," U.S. Pat. Pub. No. 2010/0249677 filed Mar. 26, 2010 and entitled "Piezoelectric Stimulation Device," U.S. Pat. Pub. No. 2005/0288740 filed Jun. 24, 2004 and entitled, "Low Frequency Transcutaneous Telemetry To Implanted Medical Device," U.S. Pat. No. 7,599,743 filed Jun. 24, 2004 and entitled "Low Frequency Transcutaneous Energy Transfer To Implanted Medical Device," U.S. Pat. No. 7,599,744 filed Jun. 24, 2004 and entitled "Transcutaneous Energy Transfer Primary Coil With A High Aspect Ferrite Core," U.S. Pat. No. 7,191,007 filed Jun. 24, 2004 and entitled "Spatially Decoupled Twin Secondary Coils For Optimizing Transcutaneous Energy Transfer (TET) Power Transfer Characteristics," and European Pat. Pub. No. 377695 published as International Pat. Pub. No. WO1989011701 published Nov. 30, 2004 and entitled "Interrogation And Remote Control Device."

In use, at least one electrode of an implantable electrical stimulation device can be placed in the area of a BAT depot and be coupled to a signal generator. As will be appreciated by a person skilled in the art, the signal generator can have a variety of sizes, shapes, and configurations, and can be external to the patient or implanted therein similar to a cardiac pacemaker. The signal generator can create the electrical signal to be delivered to the BAT and can be on continuously once activated, e.g., manually, automatically, etc. The signal generator can be in electronic communication with a device external to the patient's skin to turn it on and off, adjust signal characteristics, etc. The external device can be positioned near the patient's skin, e.g., using a belt, a necklace, a shirt or other clothing item, furniture or furnishings such as a chair or a pillow, or can be a distance away from the patient's skin, such as a source located elsewhere in the same room or the same building as the patient. The electrical stimulation device can include circuitry configured to control an activation distance, e.g., how close to a power source the electrical stimulation device must be to be powered on and/or begin delivering electrical signals. Correspondingly, the external device can include a transmitter configured to transmit a signal to the electrical stimulation device's circuitry. If implanted, the signal generator can include an internal power source, e.g., a battery, a capacitor, stimulating electrodes, a kinetic energy source such as magnets positioned within wired coils configured to generate an electrical signal within the coils when shaken or otherwise moved, etc. In one embodiment, a battery can include a flexible battery, such as a Flexion battery available from Solicore, Inc. of Lakeland, Fla. In another embodiment, a battery can include an injectable nanomaterial battery. The power source can be configured to be recharged by transcutaneous means, e.g., through transcutaneous energy transfer (TET) or inductive coupling coil, and/or can be configured to provide power for an extended period of time, e.g., months or years, regardless of how long the power source is intended to provide power to the device. In some embodiments, a power source can be configured to provide power for less than an extended period of time, e.g., about 7 days, such as if a battery is replaceable or rechargeable and/or if device real estate can be conserved using a smaller, lower power battery. In some embodiments, the signal generator can include an electrode patch onboard configured to generate a pulse, thereby eliminating a need for a battery.

The signal generator, and/or any other portion of the device or external device, as will be appreciated by a person skilled in the art, can be configured to measure and record one or more physical signals relating to the activation of BAT. For non-limiting example, the physical signals can include voltage, current, impedance, temperature, time, moisture, salinity, pH, concentration of hormones or other chemicals, etc. The recorded physical signals can be presented to the patient's physician for evaluation of system performance and efficacy of brown adipose activation. Also, the recorded physical signals can be used in a closed-loop feedback configuration to allow the device, e.g., the controller, to dynamically adjust the electrical signal settings used for treatment.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device."

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A medical method, comprising:
   assessing a patient to locate a depot of brown adipose tissue and then attaching at least one electrode to an area of the patient proximate to the depot of brown adipose tissue of the patient;
   generating an electrical signal;
   supplying the generated electrical signal to the at least one electrode; and
   delivering, via the at least one electrode, the electrical signal to the patient, thereby activating the brown adipose tissue and increasing energy expenditure of the brown adipose tissue, wherein the delivering includes continuously delivering the electrical signal to the patient for at least one day.

2. The method of claim 1, wherein the attaching includes implanting the at least one electrode within the patient.

3. The method of claim 1, wherein the attaching includes securing the at least one electrode in position with the at least one electrode being located external to the patient.

4. The method of claim 1, wherein the electrical signal has an activation signal pulse frequency in a range of 0.1 to 40 Hz and has a pulse width in a range of 0.1 to 1 ms.

5. The method of claim 1, wherein the electrical signal is either monophasic or bi-phasic.

6. The method of claim 1, further comprising attaching a signal generator to the patient, the signal generator generating the electrical signal.

7. The method of claim 6, further comprising implanting a power source within the patient, the power source supplying power to the signal generator.

8. The method of claim 6, further comprising supplying power to the signal generator from a power source located entirely outside the patient.

9. The method of claim 1, wherein the delivering includes continuously delivering the electrical signal to the patient for at least one week.

10. The method of claim 1, wherein the at least one electrode includes a plurality of electrodes.

11. A medical method, comprising:
    assessing a patient to locate a depot of brown adipose tissue and then positioning a device proximate to the depot of brown adipose tissue of the patient such that an electrode of the device is proximate to the depot of brown adipose tissue, the device having an active state in which the device is continuously delivering an electrical signal via the electrode and an inactive state in which the device is not delivering the electrical signal; and
    switching the device positioned proximate to the depot of brown adipose tissue from the inactive state to the active state, thereby causing electrical stimulation of the brown adipose tissue wherein the device is switched to remain in the active state for a predetermined amount of time, the predetermined amount of time being in a range of one day to four weeks.

12. The method of claim 11, wherein the positioning includes implanting only a partial portion of the device within the patient.

13. The method of claim 11, wherein the positioning includes implanting an entirety of the electrode within the patient.

14. The method of claim 11, wherein the positioning includes securing the electrode in position with at least the electrode of the device located external to the patient.

15. The method of claim 11, wherein the electrical signal has an activation signal pulse frequency in a range of 0.1 to 40 Hz and has a pulse width in a range of 0.1 to 1 ms.

16. The method of claim 11, wherein the electrical signal is either monophasic or bi-phasic.

17. The method of claim 11, wherein the switching includes starting generation of the electrical signal by a generator of the device.

18. The method of claim 11, further comprising, after the switching, changing the device from the active state to the inactive state, thereby stopping the electrical stimulation of the brown adipose tissue.

19. The method of claim 11, wherein the predetermined amount of time is in a range of one week to four weeks.

20. The method of claim 11, wherein the device includes a generator configured to generate the electrical signal, and a controller configured to control the switching of the device from inactive state to the active state.

21. The method of claim 20, wherein the positioning includes implanting the electrode within the patient, and wherein the generator is located external to the patient.

22. The method of claim 11, wherein the electrode includes a plurality of electrodes.

23. The method of claim 11, wherein assessing the patient includes at least one of imaging the patient and exposing the patient to cold temperature.

24. A medical method, comprising:
assessing a patient to locate a depot of brown adipose tissue and then attaching a device to the patient proximate to the depot of brown adipose tissue of the patient, the attaching including positioning at least a stimulating portion of the device within the patient; and
activating the device to deliver an electrical signal to the patient from the stimulating portion of the device located within the patient, thereby activating the brown adipose tissue and increasing energy expenditure of the brown adipose tissue, wherein the electrical signal is continuously delivered to the patient for an amount of time in a range of one day to four weeks.

25. The method of claim 24, wherein the attaching includes implanting the stimulating portion of the device within the patient and securing a second portion of the device external to the patient.

26. The method of claim 25, wherein the stimulating and second portions of the device are in wireless electronic communication without being physically connected together.

27. The method of claim 25, wherein the stimulating and second portions of the device are physically connected together.

28. The method of claim 24, wherein the stimulating portion of the device includes at least one electrode.

29. The method of claim 24, wherein the stimulating portion of the device includes a piezoelectric element.

30. The method of claim 24, wherein the electrical signal has an activation signal pulse frequency in a range of 0.1 to 40 Hz and has a pulse width in a range of 0.1 to 1 ms.

31. The method of claim 24, wherein the electrical signal is either monophasic or bi-phasic.

32. The method of claim 24, wherein the device comprises:
at least one electrode forming at least a portion of the stimulating portion, the at least one electrode delivering the electrical signal to the patient; and
a signal generator that is in electronic communication with the at least one electrode and that generates the electrical signal.

33. The method of claim 32, wherein the device comprises a power source configured to provide power to the signal generator, and the attaching includes positioning the power source external to the patient.

34. The method of claim 32, wherein the device comprises a power source configured to provide power to the signal generator, and the attaching includes implanting the power source within the patient.

35. The method of claim 24, wherein the electrical signal is continuously delivered to the patient for an amount of time in a range of one week to four weeks.

* * * * *